(12) United States Patent
Lei

(10) Patent No.: US 10,314,999 B1
(45) Date of Patent: Jun. 11, 2019

(54) NASAL BREATHING APPARATUS AND METHOD FOR HIGH-FLOW THERAPY AND NON-INVASIVE VENTILATION

(71) Applicant: Baiping Lei, Staten Island, NY (US)

(72) Inventor: Baiping Lei, Staten Island, NY (US)

( * ) Notice: Subject to any disclaimer, the term of this patent is extended or adjusted under 35 U.S.C. 154(b) by 0 days.

(21) Appl. No.: 16/110,570

(22) Filed: Aug. 23, 2018

(51) Int. Cl.
*A61M 16/06* (2006.01)
*A61M 16/08* (2006.01)
*A61M 16/20* (2006.01)
*A61M 16/10* (2006.01)
*A61M 16/01* (2006.01)

(52) U.S. Cl.
CPC ........ *A61M 16/0666* (2013.01); *A61M 16/01* (2013.01); *A61M 16/0672* (2014.02); *A61M 16/0683* (2013.01); *A61M 16/0688* (2014.02); *A61M 16/085* (2014.02); *A61M 16/0833* (2014.02); *A61M 16/1045* (2013.01); *A61M 16/208* (2013.01); *A61M 2205/42* (2013.01); *A61M 2230/43* (2013.01)

(58) Field of Classification Search
CPC ...... A61M 15/08; A61M 16/00; A61M 16/08; A61M 16/0816; A61M 16/0833; A61M 16/0875; A61M 16/12; A61M 16/122; A61M 16/125; A61M 16/0666; A61M 16/0672; A61M 16/06
See application file for complete search history.

(56) References Cited

U.S. PATENT DOCUMENTS

| | | | |
|---|---|---|---|
| 4,265,239 A | 5/1981 | Fischer, Jr. | |
| 4,367,735 A | 1/1983 | Dali | |
| 4,535,767 A | 8/1985 | Tiep et al. | |
| 4,989,599 A * | 2/1991 | Carter | A61M 16/0666 128/204.18 |
| 5,099,836 A * | 3/1992 | Rowland | A61M 16/0666 128/204.23 |
| 5,280,780 A | 1/1994 | Abel | |
| 5,335,656 A | 8/1994 | Bowe | |
| 5,533,506 A | 7/1996 | Wood | |
| 6,848,446 B2 | 2/2005 | Noble | |
| 7,195,018 B1 | 3/2007 | Goldstein | |
| 7,353,826 B2 | 4/2008 | Sleeper et al. | |
| 8,161,971 B2 | 4/2012 | Jaffe | |
| 8,517,022 B2 * | 8/2013 | Halling | A61M 16/0666 128/206.11 |
| 8,631,799 B2 | 1/2014 | Davenport et al. | |
| 8,707,950 B1 | 4/2014 | Rubin | |
| 9,827,392 B2 | 11/2017 | Lei | |
| 2002/0112730 A1* | 8/2002 | Dutkiewicz | A61M 16/0666 128/207.18 |

(Continued)

Primary Examiner — Michael J Tsai
(74) Attorney, Agent, or Firm — Walter J. Tencza, Jr.

(57) ABSTRACT

Nasal breathing apparatuses for delivering gases, monitoring end-tidal CO2, and providing CPAP and NIV through a patient's nose are provided, including a central tubular chamber, a pair of nasal sealing members, one or a pair of breathing tube(s), an inner central tube, one or a pair of delivery tube(s), and a pair of side straps coupled with a head strap. Inner central tube and delivery tube(s) are positioned inside central tubular chamber and breathing tube(s), respectively. Alternatively, central tubular chamber and breathing tube(s) have a double lumen configuration. The nasal breathing apparatuses are compact and lightweight and have reduced noise during use.

7 Claims, 17 Drawing Sheets

(56) References Cited

U.S. PATENT DOCUMENTS

| | | |
|---|---|---|
| 2004/0015092 A1 | 1/2004 | Pettersson |
| 2006/0107958 A1 | 5/2006 | Sleeper |
| 2008/0223375 A1 | 9/2008 | Cortez et al. |
| 2009/0000618 A1* | 1/2009 | Warren ............. A61M 16/0666 128/202.13 |
| 2009/0165799 A1* | 7/2009 | Duquette .......... A61M 16/0666 128/204.25 |
| 2010/0252037 A1 | 10/2010 | Wondka |
| 2011/0009763 A1 | 1/2011 | Levitsky |
| 2011/0214676 A1 | 9/2011 | Allum |
| 2012/0204870 A1 | 8/2012 | McAuley |
| 2012/0255553 A1 | 10/2012 | Wood |
| 2013/0160772 A1 | 6/2013 | Tabrizchi |
| 2014/0018691 A1 | 1/2014 | McNeil |
| 2014/0066801 A1 | 3/2014 | Tero |
| 2014/0166009 A1* | 6/2014 | Flanagan .......... A61M 16/0677 128/203.22 |
| 2014/0276169 A1 | 9/2014 | Chua |
| 2014/0366880 A1 | 12/2014 | Metz |
| 2015/0000654 A1* | 1/2015 | Martin ................. A61M 16/12 128/203.12 |
| 2015/0013678 A1 | 1/2015 | McAuley et al. |
| 2015/0230731 A1 | 8/2015 | Levitsky et al. |
| 2016/0158476 A1 | 6/2016 | Tatkov |
| 2017/0203070 A1 | 7/2017 | Lei |

* cited by examiner

Fig. 5A
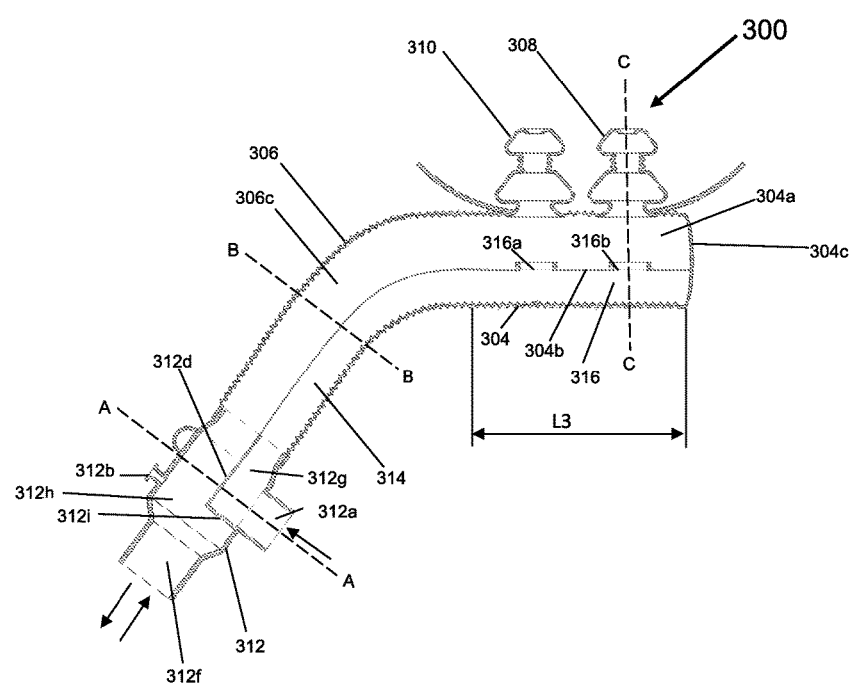
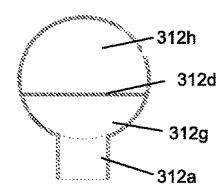
SECTION A-A
Fig. 5B
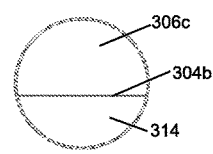
SECTION B-B
Fig. 5C
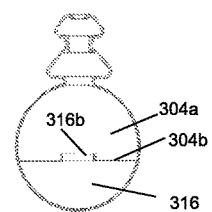
SECTION C-C
Fig. 5D

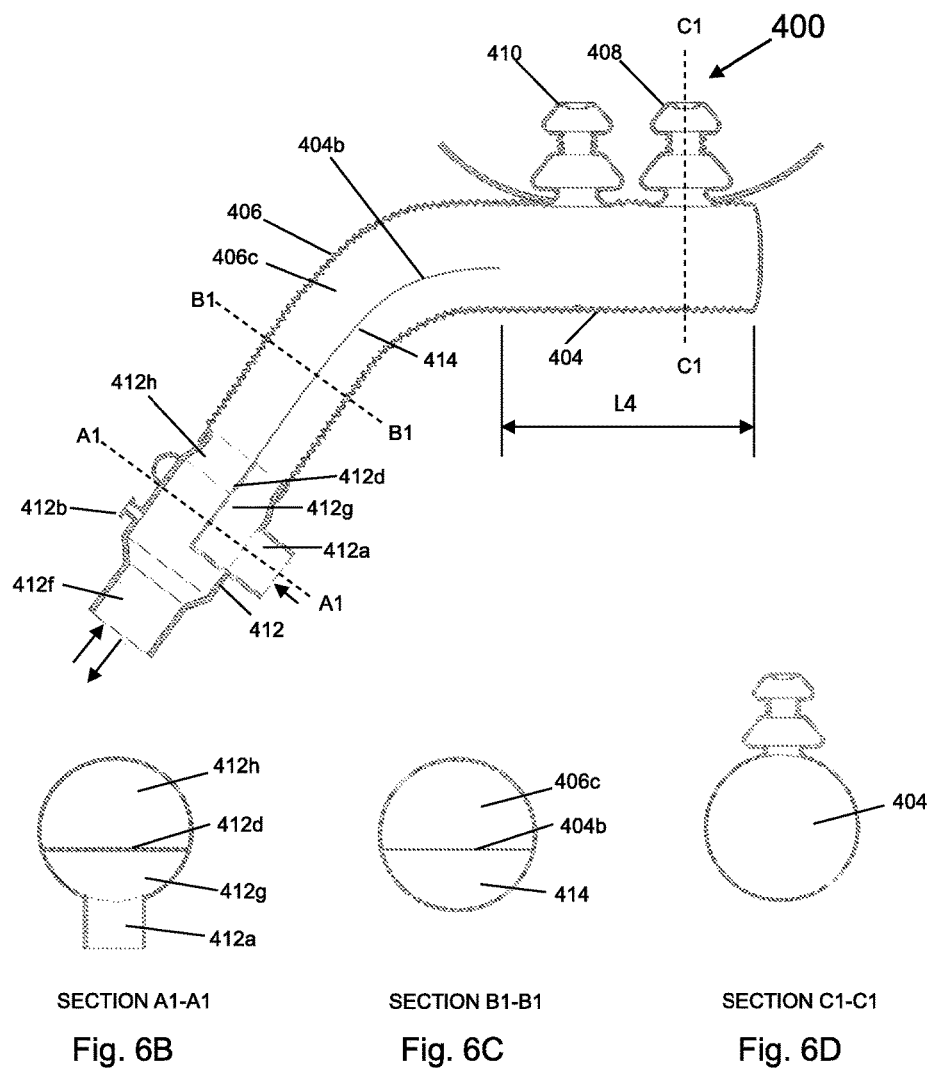

SECTION A3-A3

SECTION B3-B3

SECTION C3-C3

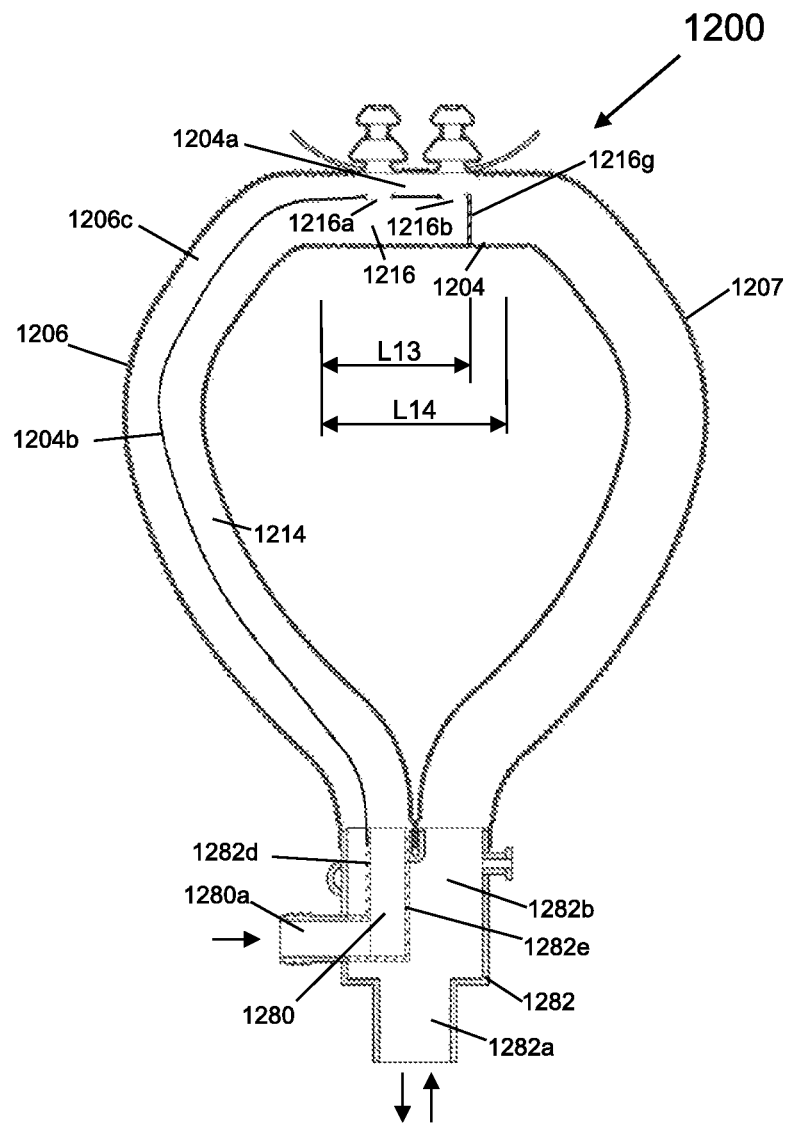

NASAL BREATHING APPARATUS AND METHOD FOR HIGH-FLOW THERAPY AND NON-INVASIVE VENTILATION

FIELD OF THE INVENTION

The present invention relates generally to the field of respiratory therapy and anesthesia. More particularly, the present invention relates to apparatus and methods for delivering high flow of gases and providing continuous positive airway pressure and non-invasive ventilation to a patient through the nose.

BACKGROUND OF THE INVENTION

Hypoventilation and apnea are the most common causes of hypoxemia in perioperative patients. Supplementing oxygen and/or providing mechanical ventilation (non-invasive or invasive) is an essential approach to correcting hypoxemia and avoiding serious consequences associated with hypoxemia. Currently, oxygen supplementation is usually achieved through either a nasal cannula or a face mask (including simple face mask, partial rebreathing face mask, nonrebreathing face mask, Venturi mask, face oxygen tent). Nasal cannulas and face masks are very useful in patients who have mild respiratory depression or in patients who do not have respiratory depression but have other medical conditions that can cause hypoxemia. In patients with hypoventilation and apnea, mechanical ventilation (non-invasive or invasive) is the most effective approach to achieve adequate ventilation and to correct hypoxemia. Non-invasive ventilation (NIV) is usually used first to achieve adequate ventilation and oxygenation prior to endotracheal intubation (invasive ventilation). However, existing conventional nasal cannulas and face masks can only be used for delivering oxygen and cannot be used for NIV. To perform NIV, the nasal cannula or the face mask must be removed first and then a ventilation face mask or nasal mask will be placed on a patient's face or nose. Once the patient's condition improves and the patient regains the ability to maintain adequate spontaneous ventilation and oxygenation, the ventilation face mask or nasal mask will be replaced with a conventional nasal cannula or face mask in order to maintain adequate oxygenation. It is inconvenient to frequently switch back and forth between a conventional nasal cannula or face mask and a ventilation face or nasal mask, especially in patients with labile respiratory function.

Recently, high-flow nasal cannula (HFNC) oxygen delivery has been gaining attention for critically ill patients who are not candidates for NIV. HFNC has been shown to decrease the frequency and the work of breathing and reduce needs for escalation of respiratory support in patients with diverse underlying diseases such as hypoxemic respiratory failure, acute exacerbation of chronic obstructive pulmonary disease (COPD) and acute heart failure. There are several HFNCs available in the market. They include Optiflow (trademark) HFNC (manufactured by Fisher&Paykel Healthcare Inc), Vapotherm HI-VNI (trademark) (manufactured by Vapotherm Inc), AquaNASE (trademark) nasal cannula (manufactured by Armstrong Medical, Inc), and ACUCARE (trademark) (manufactured by ResMed, Inc). They can deliver a heated and humidified air/oxygen at a flow rate of up to 60 liters per minute (lpm). The patient interfaces have two enlarged nasal prongs that are placed in a patient's nostrils, but the nasal prongs do not create a seal between the nasal prongs and the nares. Thus, HFNC cannot actively enhance tidal volume. None of the existing HFNCs can be used for NIV because they neither push during inspiration nor pull during expiration. To perform NIV, HFNC must be removed and a ventilation face mask or nasal mask will be placed on a patient's face or nose. Since HFNC is usually used for critically ill patients who are otherwise the candidates for NIV or invasive ventilation, switching between high-flow oxygen therapy and NIV will become even more frequent. Thus, there is a need for a patient interface that can be used for both high-flow oxygen therapy and NIV so that high-flow oxygen therapy and NIV can be switched without changing the patient interface.

NIV means ventilatory support without an endotracheal or tracheotomy tube. It has been widely used to treat acute or chronic respiratory failure and has been considered the standard care for acute exacerbations of COPD and severe acute cardiogenic pulmonary edema. Clinical studies have demonstrated that NIV is equivalent in efficacy to conventional mechanical ventilation. NIV has been also applied to prevent or to treat perioperative respiratory failure. It is particularly useful in patients at high risk of postoperative respiratory failure such as morbid obese, preexisting lung diseases, thoracic and cardiac surgeries, and upper abdominal surgery. The use of NIV has been shown to effectively prevent or treat acute respiratory failure and to avoid endotracheal intubation in the post-operative period. The benefits of NIV include lower complication rates, shorter duration of hospital stay, lesser cost of treatment, and reduced morbidity and mortality rates.

However, NIV has a very high failure rate, ranging between 18% and 40% in the acute setting. Although the success of NIV depends on many factors, such as patient selection, underlying pathology, the severity of acute respiratory failure, and expertise with NIV, interface choice is one of the key factors determining the success of NIV. The commonly used interfaces for NIV include nasal masks, orofacial masks, full face masks, mouthpieces, nasal pillows, and helmets. Each of them has its own advantages and disadvantages and clinical trials have not demonstrated the superiority of any interface. The common problems associated with orofacial masks and nasal masks include air leaks, noise, discomfort, skin lesions, and conjunctivitis. These problems are the common reasons for poor patient compliance and high NIV failure rates. To overcome interface-related problems and increase patient compliance, several nasal interfaces have been manufactured to replace nasal or face masks for attaining CPAP and NIV. These nasal interfaces include Nasal Aire II (trademarked) (manufactured by InnoMed Technologies, Inc), Bravo (trademarked) nasal pillow CPAP mask (manufactured by InnoMed Technologies, Inc), Swift TM FX (trademarked) nasal pillow (manufactured by ResMed, Inc) and AirFit P10 (trademarked) nasal pillow (ResMed, Inc). They completely seal the nostrils and prevent air leakage during inhalation and exhalation. These nasal interfaces are more comfortable to wear and have increased patient comfort and compliance. However, there are still some drawbacks with the existing nasal interfaces. First, the existing nasal interfaces seal the nostrils by forming airtight barriers either inside the nostrils or outside the nostrils. None of them provide airtight seal in both inside and outside the nostrils. Thus, excessive pressure must be applied to the nose to prevent air leaking, which causes significant discomfort for patients. Secondly, the existing nasal interfaces use single limb patient circuits for delivering gases from the flow generator or ventilator to the nasal interfaces, and require exhaust or vent holes at, near or adjacent to the nasal interfaces for discharging the patient's expired breathing gases. Thus, gases are continuously leaking through the exhaust or vent holes during use. This continuous air leaking through the exhaust or vent holes has several disadvantages: 1) high flow rates are needed to compensate for air leaks; 2) larger patient circuits are needed to deliver high flow of gases from the ventilator to the patient interfaces; 3) the air exhaust through the exhaust or vent holes creates a loud noise which is disturbing and irritating the patients during use. Thirdly, the patients cannot breathe naturally and have difficulty breathing out during exhalation because a minimum-required pressure of 4 centimeters of water ($cmH_2O$) is constantly provided during use in order to facilitate discharging the expired gases. Thus, there is a need for a patient interface that can be used for CPAP and NIV with less airflow and reduced noise level.

U.S. Pat. No. 6,679,265, issued Jan. 20, 2004 to Strickland and Lee discloses a patient interface which includes a pair of nasal inserts which are fed bilaterally by a pair of delivery tubes. The nasal inserts seal the nostrils by forming airtight barriers inside the nostrils and a simple head strap is used to support the interface. The device of Strickland and Lee is lightweight and more comfortable to wear. However, like all other existing nasal interfaces, the exhaust ports are positioned near the nose and the delivered gases will continuously leak through the exhaust ports during inhalation and exhalation. The patient cannot inspire air from the outside of the interface during inhalation and all airflow is supplied by a flow generator. Thus, high flow rates are required to obtain the desired therapeutic pressures. Furthermore, the air exhaust through the exhaust ports constantly makes a loud noise during use and the interface is not ideal for delivering gases and monitoring end tidal carbon dioxide ($EtCO_2$) when NIV is not needed.

Thus, there is a need for an improvement which overcomes the aforementioned problems of the prior art devices and provides a nasal interface that can be used for both delivering high flow of gases and providing CPAP and NIV and that improves patient comfort and increases patient compliance.

SUMMARY OF THE INVENTION

One or more embodiments of the present invention provide one or more devices and methods for delivering gases, monitoring $EtCO_2$, and providing CPAP and NIV.

It is an object of one or more embodiments of the present invention to provide a simple, disposable, and inexpensive nasal breathing apparatus and method that can be used in majority of inpatients or ambulatory patients for delivery of gases, spontaneous respiration monitoring, CPAP, and NIV.

It is another object of one or more embodiments of the present invention to provide a nasal breathing apparatus that is compact, lightweight, disposable, and inexpensive. In accordance with one embodiment of the present invention, the main components of the nasal breathing apparatus are made integrally and formed as a single piece. There are no connectors or joints at, or near the nose or the face. The breathing tube and the delivery tube are coaxially arranged as a single assembly. In accordance with another embodiment of the present invention, the breathing tube is made as a single double lumen tube, thus reducing the weight and the bulkiness of the device. The devices of the present invention are compact and lightweight so that there is no need for a heavy headgear to support the nasal breathing apparatus. The device of the present invention can be held in place with a simple head strap. Thus, the use of the device of the present invention will increase the comfort of patients and decrease the chance of infection.

It is another object of one or more embodiments of the present invention to provide a nasal breathing apparatus that can reliably seal the nostrils without applying significant pressure on the nose. In accordance with one embodiment of the present invention, the nasal breathing apparatus has a pair of nasal sealing members which not only form airtight barriers inside the corresponding nostrils, but also seal the openings of the corresponding nostrils. Each nasal sealing member is comprised of a top portion which is constructed in a way that can fit snugly inside the nostrils of a patient and form an airtight barrier in the corresponding nostrils and a base portion which is constructed in a way that can seal the openings of the corresponding nostrils when the top portions of the nasal sealing members are placed inside the nostrils. Both the top portions and the base portions of the nasal sealing members are constructed in mushroom shapes which are soft, thin-walled, resilient, and deformable. This configuration allows to seal different sized and different shaped nostrils and to have a large internal diameter which permits to deliver gases to and discharge gases from the nasal passages without significant resistance. The dual seal feature permits to have an adequate seal without pressure or with only minimal pressure on the nose when the nasal breathing apparatus used for oxygen delivery and to attain a maximum seal when the nasal breathing apparatus used for CPAP and NIV.

It is another object of one or more embodiments of the present invention to provide a nasal breathing apparatus that the pressure applied by the nasal sealing members on the nose can be adjusted according to the patient's need. In accordance with one embodiment of the present invention, the nasal breathing apparatus has two side straps which are positioned between the bottoms of the base portions of the nasal sealing members and a top wall of the central tubular chamber. Each side strap is extended laterally from the corresponding base portions of the nasal sealing members and coupled to a head strap. By adjusting the head strap, the pressure applied by the side straps on the nasal sealing members and the nose can be adjusted according to the patient's need. If NIV or CPAP is not needed, only the top portions of the nasal sealing members seal the inside of the nostrils and there will be no pressure or minimal pressure on the nose. This will provide a great flexibility and optimal comfort for patients in both short and long-term therapies.

It is another object of one or more embodiments of the present invention to provide a nasal breathing apparatus that has reduced jet effects on the patient's nasal passages during gases delivery. In accordance with one embodiment of the present invention, the nasal breathing apparatus of the present invention has an inner central tube. The inner central tube is located inside the central tubular chamber and laterally connected to a delivery tube which is located inside the breathing tube. The inner central tube has two holes or ports that are axially aligned with the corresponding nasal sealing members to direct airflow toward the nasal sealing members and the combined inner diameter of the two holes or ports is larger than the inner diameter of the inner central tube. Thus, the velocity will be decreased when the delivered gases from the delivery tube pass through the holes or ports of the inner central tube. Furthermore, the velocity of the delivered gases further decreases when they pass through the nasal sealing members because the mushroom-shaped base portions and top portions are also larger than the holes or ports of the inner central tube in diameter. The decreased velocity will decrease jet effects and noise and will increase the comfort of patients.

It is another object of one or more embodiments of the present invention to provide a nasal breathing apparatus that can be used for continuous oxygenation and ventilation in patients whose mouth must be left open during the procedures. In accordance with one embodiment of the present invention, the nasal breathing apparatus has a central tubular chamber which is fluidly connected to the nasal sealing members and a breathing tube. The breathing tube is connected to the central tubular chamber leftwardly or rightwardly and positioned away from the mouth. The central tubular chamber is made in a size which allows to be placed beneath the nose and above the upper lip of the mouth so that the nasal breathing apparatus will not interfere with manipulations in the mouth. The nasal breathing apparatus can be used for preoxygenation, apneic oxygenation, and ventilation in patients who are undergoing general anesthesia or who are undergoing the procedures in which the mouth must be left open such as endotracheal intubation, upper endoscopy, bronchoscopy, and transesophageal echocardiography. Oxygen can be delivered to the nasal airway via the delivery tube or the outlet of the coupler when the patient breathes spontaneously. The patient can talk and communicate with the anesthesiologists. This will greatly reduce patient anxiety and enhance comfort. The patient will be more likely willing to wear the device. NIV can be initiated by connecting an anesthesia circuit or a resuscitator bag to the outlet of the coupler when the patient goes asleep and stops breathing. Oxygen can also be continuously delivered to the nasal airway via the device or even NIV can be continued via the nose during manipulation for endotracheal intubation or other procedures in which the mouth must be left open. Continuing NIV or supplementing high-flow oxygen during endotracheal intubation will significantly reduce the incidents of hypoxemia during anesthesia induction and endotracheal intubation and increase patient safety. Furthermore, the same device can be used during patient transportation after the procedure and in post anesthesia care unit (PACU) for oxygen delivery and possible NIV. Additional nasal cannula or face mask is not needed. This will be more convenient and will also reduce hospital costs.

It is an object of one or more embodiments of the present invention to provide a nasal breathing apparatus that can be used for high-flow oxygen therapy through the sealed nostrils. At least one embodiment of the present invention provides a device with a pair of nasal sealing members, a central tubular chamber, an inner central tube, a delivery tube for delivering gases, and a breathing tube for delivering and discharging gases. The central tubular chamber and the breathing tube permit the patient to breathe through the sealed nostrils in a normal breathing pattern. Since the gas flow through the nostrils is not obstructed, the patient will feel more comfortable when wearing the nasal breathing apparatus of the present invention. The oxygen flow rate can reach up to 25 lpm with a single oxygen supplying source such as a conventional wall oxygen flow meter, an oxygen tank, or an anesthesia machine. The gas flow rate can reach up to 60 lpm with an air/oxygen blender and a heated humidifier. Since there is no leakage of oxygen from the nose, in one or more embodiments, a much lower flow rate of oxygen is needed for achieving nasal insufflation. When NIV is needed, the outlet of the coupler can be connected to an anesthesia circuit, a ventilator, or a resuscitator bag. Thus, one can switch between high-flow oxygen therapy and NIV without changing the patient interface. Even high-flow oxygen therapy and NIV can be administered simultaneously.

It is another object of one or more embodiments of the present invention to provide a nasal breathing apparatus and method that can be used for gases delivery, spontaneous respiration monitoring, and NIV. In accordance with one embodiment of the present invention, an apparatus is provided comprising a main piece of apparatus having a pair of nasal sealing members, one central tubular chamber, one inner central tube, one delivery tube, one breathing tube, and one coupler. The delivery tube and the breathing tube are arranged coaxially in which the delivery tube is located inside the breathing tube for delivering gases. The breathing tube and the delivery tube are connected to the central tubular chamber and the inner central tube laterally (either left side or right side), respectively. The coupler is connected to the breathing tube and the delivery tube and has an outlet for delivering gases to and/or discharging gases from a patient and a port for sampling gases. When NIV is not needed, the device can be used for delivering oxygen or gases into the nasal airway from the delivery tube via the nasal sealing members. The exhaled gases are discharged into ambient from the nasal sealing members via the breathing tube and the outlet of the coupler. The patient can talk, cough, and expectorate. When the patient develops hypoventilation or apnea and ventilatory support is required to maintain adequate oxygenation and ventilation, NIV can be initiated immediately by connecting an anesthesia circuit, a ventilator, or a resuscitator bag to the outlet of the coupler. Additional face mask or nasal mask is not needed. It is very useful in patients with labile respiratory function. Since there is no need to switch interfaces for NIV, it is more convenient for both patients and clinicians. The device can be widely used in intensive care units (ICUs), emergency departments, operative rooms, PACU, step-down units, and respiratory wards.

It is another object of one or more embodiments of the present invention to provide a nasal breathing apparatus that can be used for attaining CPAP with less airflow and reduced noise levels. With a device in accordance with one or more embodiments of the present invention, a reliable seal at high therapy pressures can be attained. The nasal interface of the present invention features a dual seal at the nostrils and will have less air leaks even at maximum therapy pressures. The presence of the breathing tube or the breathing lumen eliminates the need for exhaust or vent holes on the central tubular chamber and allows the patient to inspire air from the ambient during inhalation. There is no air leaking through the central tubular chamber itself during use. Thus, the flow rate that is required for the desired therapeutic pressure will be significantly reduced. Furthermore, the use of a non-rebreathing tee adaptor allows ambient air to enter the breathing tube during inhalation and can provide adjustable resistance to expiratory airflow during exhalation, which will further reduce the flow rate that is required for attaining a desired CPAP level. The reduced flow rate will reduce the noise level that is generated by the nasal breathing apparatus (the airflow through the nasal breathing apparatus results in less turbulence and interference with the nasal breathing apparatus) and will reduce power consumption of a flow generator. The outlet of the coupler has a large diameter and is placed far away from the ears. The coupler also can be connected to a vent tube. The outlet of the vent tube can be placed at a remote location from the face. Thus, the noise level from the exhaust gases will be significantly reduced during CPAP therapy. The use of the single limb coaxial breathing tube or the single limb double lumen breathing tube not only makes the nasal interface more compact and lightweight, but also helps reduce heat loss and maintain humidity of the inspired gases. It is more comfort to wear and more likely accepted by the patients. It will greatly enhance patient comfort and compliance.

It is another object of one or more embodiments of the present invention to provide a device that can be used for anesthesia induction and/or maintenance for short surgical procedures or office-based anesthesia such as in a dental office. With a device in accordance with one or more embodiments of the present invention, an anesthesia circuit can be attached to the outlet of the coupler. Inhalational agents (such as nitrous oxide or sevoflurane) can be delivered into the airway via the nose without using a face mask. The patient can talk and communicate with the anesthesiologists during anesthesia induction. It may be more easily applied and more likely accepted by patients, especially children. The adequate level of anesthesia can be easily maintained, and the patient's respiration can be continuously monitored by monitoring $EtCO_2$ during the procedure. Since there is no leakage of gases from the nose and the excessive delivered gases can be easily scavenged, in one or more embodiments, it will also reduce anesthetic air pollution.

It is yet another object of one or more embodiments of the present invention to provide a device that can be used for NIV. By connecting a ventilator or a resuscitator bag to the outlet of the coupler, NIV can be initiated without a nasal or face mask. Since the device provides dual seals at the nostrils, a constant and reliable seal can be obtained even under high pressures. The use of the device of one or more embodiments of the present invention will enhance the likelihood of successful NIV and reduce the need for intubation or reintubation.

BRIEF DESCRIPTION OF THE DRAWINGS

FIG. 5A shows a simplified diagram of a front cross-sectional view of part of the nasal breathing apparatus, somewhat different from that in FIG. 1, in accordance with another embodiment of the present invention;

FIG. 5B shows a cross-sectional view of the nasal breathing apparatus of FIG. 5A along a line A-A;

FIG. 5C shows a cross-sectional view of the nasal breathing apparatus of FIG. 5A along a line B-B;

FIG. 5D shows a cross-sectional view of the nasal breathing apparatus of FIG. 5A along a line C-C;

FIG. 6A shows a simplified diagram of a front cross-sectional view of part of the nasal breathing apparatus, somewhat different from that in FIG. 1, in accordance with another embodiment of the present invention;

FIG. 6B shows a cross-sectional view of the nasal breathing apparatus of FIG. 6A along a line A1-A1;

FIG. 6C shows a cross-sectional view of the nasal breathing apparatus of FIG. 6A along a line B1-B1;

FIG. 6D shows a cross-sectional view of the nasal breathing apparatus of FIG. 6A along a line C1-C1;

FIG. 16 shows a simplified diagram of a front cross-sectional view of part of the nasal breathing apparatus, somewhat different from that in FIG. 12, in accordance with another embodiment of the present invention.

DETAILED DESCRIPTION OF THE DRAWINGS

In order to assist in the understanding of the features and advantages of embodiments of the present invention, the following detailed description of the exemplary embodiments should be considered in conjunction with the accompanying drawings. One or more embodiments of the present invention provide a novel nasal breathing device that can be used for delivering gases, monitoring exhaled gases, and providing CPAP (continuous positive airway pressure) and NIV (non-invasive ventilation). The preferred embodiments of the present invention will now be described with reference to the drawings. The drawings are not necessarily to scale and mainly used to illustrate principles of the present invention.

Figure 1:
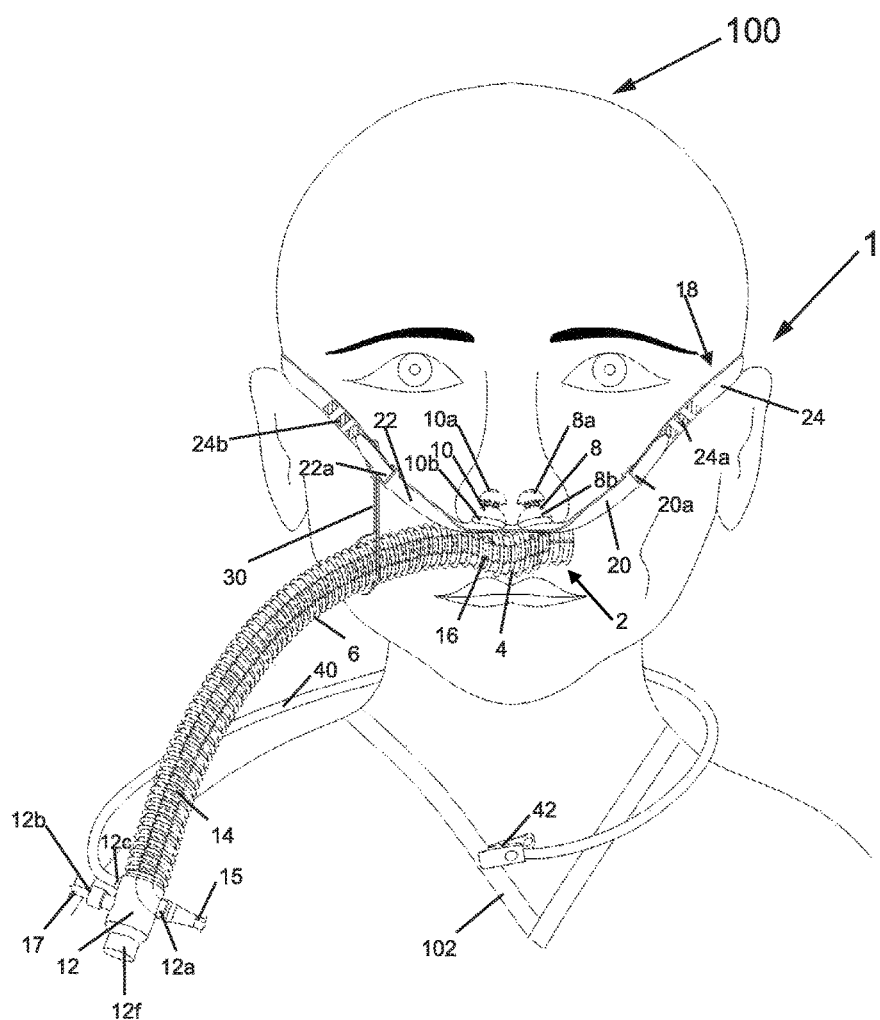
FIG. 1 shows a simplified diagram of a front view of a nasal breathing apparatus in accordance with an embodiment of the present invention being worn by a patient.

With reference to FIG. 1, an apparatus 1 of the first embodiment of the present invention is shown in which a patient or person 100 is wearing the apparatus 1. The apparatus 1 includes a main portion 2 and a head strap system 18.

The main portion 2 is placed on the face of the patient or person 100 and a central tubular chamber 4 is beneath the nose and above the upper lip of the mouth of the patient or person 100 and is secured on the face of the patient or person 100 with a head strap 24 placed around the back of the head and above the ears. The head strap 24 is tightened to maintain adequate pressure on the nose and the face to prevent air leaking from the nostrils and hold the device or apparatus 1 in position to prevent falling from the face. A breathing tube strap 30 is looped around the breathing tube 6 near the right end of the central tubular chamber 4 and the right side of the head strap 24 for holding the breathing tube 6 away from the mouth and preventing the breathing tube 6 from pulling the central tubular chamber 4 away from the nose. A top portion 8a of a first nasal sealing member 8 is placed in the left nostril (on the patient's left, on the right of FIG. 1) and a top portion 10a of a second nasal sealing member 10 in the right nostril (on the patient's right, on the left of FIG. 1). The top portions 8a and 10a of the nasal sealing members 8 and 10, respectively, form an airtight barrier inside the corresponding nostrils. Base portions 8b and 10b of the nasal sealing members 8 and 10 seal the openings of the corresponding nostrils, respectively. Gases are continuously delivered to the nasal airway from the gas supplying port 12a of the coupler 12 via the delivery tube 14 which is positioned inside the breathing tube 6, the inner central tube 16, the central tubular chamber 4, and the nasal sealing members 8 and 10 during inhalation and exhalation. The exhaled gases from both nasal sealing members 8 and 10 and the excessive gases from the inner central tube 16 are discharged into the ambient air through the breathing tube 6 and the outlet 12f of the coupler 12 and sampled via the sampling port 12b of the coupler 12. The patient or person 100 can breathe in and out through the breathing tube 6 during spontaneous respiration. A neck strap 40 has one end which is attached to the half ring 12c on the coupler 12 and an opposing end which has a badge clip 42 that is attached to the patient's neck collar 102 or the clothes of the person 100. The length of the neck strap 40 can be adjusted to hold the coupler 12 in place so that the coupler 12, the gas sampling tubing 17, and the gas supplying tubing 15, will not pull the breathing tube 6 and the central tubular chamber 4 away from the face resulting from their weight.

Figure 2A:
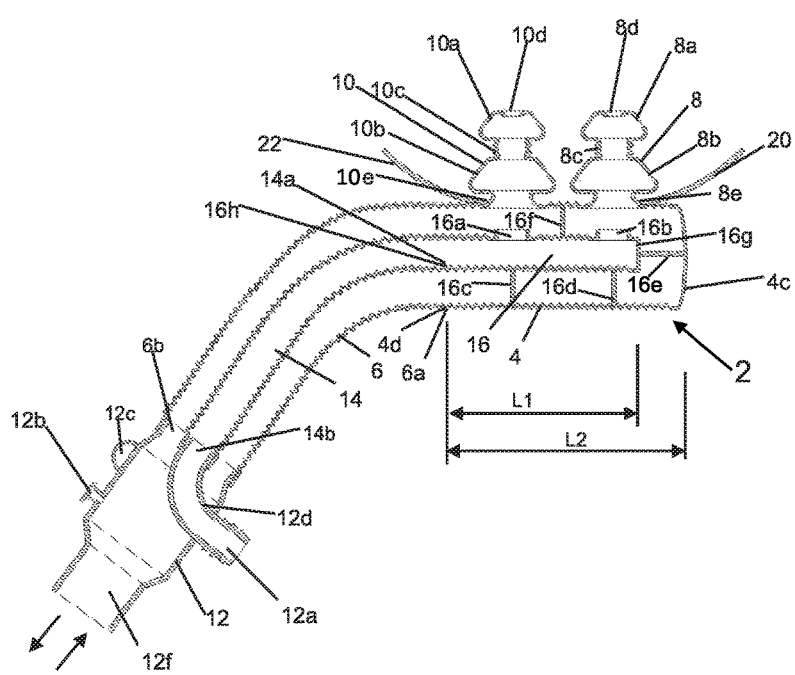
FIG. 2A shows a simplified diagram of a front cross-sectional view of part of the nasal breathing apparatus of FIG. 1.

FIG. 2A shows a simplified diagram of a front cross-sectional view of part of the nasal breathing apparatus 1 of FIG. 1. The main portion 2 of the apparatus 1 includes a first nasal sealing member 8, a second nasal sealing member 10, a central tubular chamber 4, an inner central tube 16, a breathing tube 6, a delivery tube 14, and a coupler 12. The central tubular chamber 4 is in fluid communication with the nasal sealing members 8 and 10, the inner central tube 16, the breathing tube 6, the delivery tube 14, and the coupler 12. The nasal sealing members 8 and 10, the central tubular chamber 4, the inner central tube 16, the delivery tube 14, and the breathing tube 6 are manufactured integrally and formed as a single piece. Alternatively, they can be made separately and molded together to form into a single piece.

Nasal sealing members 8 and 10 include top portions 8a and 10a, tubes 8c and 10c, base portions 8b and 10b, and short tubes 8e and 10e, respectively. The nasal sealing member 8 or 10 is integrally formed as a single piece. The top portion 8a or 10a and the tube 8c or 10c, in at least one or more embodiments, may be similar or identical to the top portion 114d and the tube 112, respectively, of the nasal inert 114, as shown in FIGS. 1 and 2 and in the description of FIGS. 1 and 2, of U.S. Pat. No. 9,827,392, which is incorporated by reference herein.

The nasal sealing members 8 and 10 should be soft, thin-walled, deformable, flexible, resilient, and lightweight. The top portions 8a and 10a of the nasal sealing members 8 and 10, respectively, are formed in a mushroom shape and fit into the user's corresponding nostrils as shown in FIG. 1. Each of the mushroom-shaped top portions 8a and 10a has a top, a bottom, a first opening at the top and a second opening at the bottom. The sizes of the top portions 8a and 10a may vary. The top portions 8a and 10a can be made in different sizes to fit different sized nostrils. For an adult, the bottoms of the mushroom-shaped top portions 8a and 10a preferably have an outer diameter of about ten to sixteen millimeters and the first openings at the tops preferably have a diameter of about 50% to 70% of the outer diameter of the bottoms. The length or height of the mushroom-shaped top portions 8a and 10a (the distance from the top to the bottom) preferably is equal to about 50% to 70% of the outer diameter of the bottoms of the top portions 8a and 10a. When the top portions 8a and 10a are placed into the corresponding nostrils, the bottoms of the top portions 8a and 10a, will be preferably located inside the corresponding nostrils. The first openings of the top portions 8a and 10a are preferably located in the centers of the tops of the top portions 8a and 10a and have an inward rolled rim 8d and 10d shown in FIG. 2A. The inward rolled rims 8d and 10d and the top portions 8a and 10a of both nasal sealing members 8 and 10 are made from soft, flexible, resilient, biocompatible, non-irritating materials such as silicone, thermoplastic elastomers, or the like. The thickness of the walls at the inward rolled rims 8d and 10d is preferably about 0.2 to 0.5 millimeters and thinner than the other parts of the top portions 8a and 10a. The length of the inward rolled part is about one to two millimeters so that the inward rolled rims 8d and 10d will not obstruct the first openings of the top portions 8a and 10a in case the inward rolled rims 8d and 10d are flipped forward under the positive pressure of incoming gases inside the top portions 8a and 10a of the nasal sealing members 8 and 10, respectively. The inward rolled rims 8d and 10d, in at least one embodiment, should be very soft and contact the mucous membrane of the nasal cavities in the corresponding nostrils, which form a physical sealing interface between the outer surface of the inward rolled rim 8d and 10d and the mucous membrane. The inward rolled rim configuration and the thinness and softness of the top portions 8a and 10a of the nasal sealing members 8 and 10, respectively, will make the top portions 8a and 10a less stimulating and more comfortable for wearing. As an alternative, the first openings can have an outward rolled rim (not shown). The inward or the outward rolled rim will also help maintain the shape of the mushroom-shaped top portions 8a and 10a and prevent collapse. In at least one embodiment, there will be no inward or outward rolled rim on the first openings of the mushroom-shaped top portions 8a and 10a. In at least one embodiment, the outer surface of the top portions 8a and 10a can be coated with a thin layer of silicone gels, or the like to increase comfort. The thickness of the layer of the silicone gels or the like may be 0.2 to 1.0 millimeter. The top portions 8a and 10a can comfortably fit into the user's nostrils and form a physical sealing interface between the outer surface of the top portions 8a and 10a and the inner wall of the corresponding nostrils. It prevents the dislodgement of the top portions 8a and 10a of the nasal sealing members 8 and 10 in general from the corresponding nostrils because the bottoms of the mushroom-shaped top portions 8a and 10a are larger in cross-section than the openings of the user's nostrils. The top portions 8a and 10a are compressible, deformable, and resilient allowing the bottoms of the top portions 8a and 10a to fit into the corresponding nostrils and to maintain their shapes even though the top portions 8a and 10a may be wider in width than the width of the nostrils.

It is appreciated that the top portions 8a and 10a of the nasal sealing members 8 and 10, respectively, can be formed in any other suitable shapes as long as they seal the nostrils and do not cause significant discomfort. However, a mushroom shape with an inward rolled rim 8d and 10d, such as shown in FIG. 2A, or an outward rolled rim (not shown), is preferred. The mushroom-shaped top portions 8a and 10a are gradually increased in diameter from their tops at first openings (about six to ten millimeters in outer diameter) to their bottoms (about ten to sixteen millimeters in outer diameter). The thickness of the wall of the mushroom-shaped top portions 8a and 10a is also gradually increased from the first openings (about 0.2 to 0.5 millimeters) to the bottoms (about 0.5 to 1 millimeters). The increased thickness of the bottoms of the top portions 8a and 10a will help maintain the shapes of the top portions 8a and 10a and increase the stability. It will be appreciated by one having ordinary skill in the art that the shapes and the sizes of the top portions 8a and 10a and the thickness of the wall of the top portions 8a and 10a including the inward rolled rims 8d and 10d can be varied without departing from the scope of the disclosed concept. When the top portions 8a and 10a are at least partially inserted into the nostrils, the inward rolled rims 8d and 10d may contact the inner wall of the nostrils first and form physical sealing interfaces. If the top portions 8a and 10a are further pushed into the nostrils, they always can reach a position where the cross-section of any part of the top portions 8a and 10a of the nasal sealing members 8 and 10, respectively, matches the cross-section of the nostrils and forms an airtight barrier.

The top portions 8a and 10a of the nasal sealing members 8 and 10 may be constructed of any soft non-irritating and inert material apparent to those having skill in the relevant art(s) after reading the description herein. The top portions 8a and 10a are soft, lightweight, resilient, compressible, deformable, and expandable. The top portions 8a and 10a can expand under the positive pressure of incoming gases. Thus, the top portions 8a and 10a of the nasal sealing members 8 and 10, respectively, will fit and seal different anatomical sizes and shapes for nostrils for different persons. The comfortable top portions 8a and 10a of the nasal sealing members 8 and 10, respectively, create a minimal amount pressure against the nostrils when inserted, have the ability to maintain their integrity and to significantly distort their shapes to easily conform to different nostril shapes, and provide a seal at varying depths within the nostrils without discomfort. The unique configuration of the top portions 8a and 10a will provide a very comfortable fit in the nostrils and create an airtight seal to prevent the leakage of gases from the nostrils during inspiration and expiration.

The base portions 8b and 10b of the nasal sealing members 8 and 10, respectively, are shaped into a mushroom shape. Each of the mushroom-shaped base portions 8b and 10b has a top, a bottom, a first opening at the top, and a second opening at the bottom. The mushroom-shaped base portions 8b and 10b are gradually increased in diameter from the tops to the bottoms. The mushroom-shaped base portions 8b and 10b are generally larger than the mushroom-shaped top portions 8a and 10a and should be built at a size that is large enough so that they can seal the openings of the corresponding nostrils when the top portions 8a and 10a are placed inside the corresponding nostrils. An outer diameter of the bottoms of the base portions 8b and 10b is generally about 20% to 30% larger than the outer diameter of the bottoms of the mushroom-shaped top portions 8a and 10a. The height or the depth of the mushroom-shaped base portions 8b and 10b is preferably about five to ten millimeters. The bottoms of the base portions 8b and 10b have the second openings of the base portions 8b and 10b. The second openings are preferably positioned in the center of the bottoms of the base portions 8b and 10b. The thickness of the wall of the base portions 8b and 10b is gradually increased from their tops (about 0.2 to 0.5 millimeter) to their bottoms (about 0.5 to 1 millimeter). In at least one embodiment, the base portions 8b and 10b are made more stiff or rigid than the top portions 8a and 10a so that the base portions 8b and 10b cannot be easily compressed or deformed. It will be appreciated by one having ordinary skill in the art that the wall of the base portions 8b and 10b can be varied in thickness and stiffness without departing from the scope of the disclosed concept. The outer surfaces of the base portions 8b and 10b are very soft and will not cause any discomfort or irritation when they contact the openings of the nostrils. In at least one embodiment, a thin layer of silicone gels or the like (about 0.5 to 1 millimeter) can be attached to the outer surfaces of the base portions 8b and 10b to increase the softness and comfort. The top portions 8a and 10a of the nasal sealing members 8 and 10, respectively, will form airtight sealing interfaces inside the corresponding nostrils while the base portions 8b and 10b of the nasal sealing members 8 and 10, respectively, will seal the openings of the corresponding nostrils. This dual seal configuration will provide a very good airtight seal so that the effective NIV (non-invasive ventilation) or CPAP (continuous positive airway pressure) can be achieved with the device of the present invention without applying excessive pressures on the nose. When the device of the present invention is used for delivering gases and not used for NIV or CPAP, the base portions 8b and 10b of the nasal sealing members 8 and 10 will not apply pressure on the nose. Thus, the patient will feel more comfortable when wearing the device or apparatus 1 of the present invention.

The top portions 8a and 10a of the nasal sealing members 8 and 10, respectively, are connected to the base portions 8b and 10b of the nasal sealing members 8 and 10 by tubes 8c and 10c, respectively. Each of the tubes 8c and 10c is preferably positioned in the center of the bottom of the respective top portion 8a and 10a. Each tube of tubes 8c and 10c, has a first end that is also the second opening of its corresponding top portion 8a and 10a and a second end that is also the first opening of its corresponding base portion 8b and 10b. The tubes 8c and 10c preferably have an inner diameter equal to the inner diameter of the first opening of the top portions 8a and 10a or ten to fifteen percent larger than the inner diameter of the first opening of the top portions 8a and 10a, respectively. The incoming gas flow will produce a positive pressure inside the mushroom-shaped top portions 8a and 10a and help form an airtight barrier in the nostrils. The tubes 8c and 10c, in at least one embodiment, are formed in a spirally corrugated shape. The spirally corrugated configuration will provide more flexibility and elasticity and allow adjusting the direction and position of the top portions 8a and 10a, respectively. The tubes 8c and 10c, in at least one embodiment, are flexible, shortenable, extendable, and crush-resistant. The tubes 8c and 10c are configured so that they do not cause significant discomfort even when they are pushed toward the nose forcefully because they have some buffer effects from their spirally corrugated configurations. The spirally corrugated configurations of the tubes 8c and 10c also create a slight twisting force toward the nose and help form a physical seal between the outer surface of the top portions 8a and 10a, respectively, and the inner wall of the nostrils. The thickness of the wall of each of tubes 8c and 10c is about 0.5 to 1.0 millimeters. The length of each of the tubes 8c and 10c will be short and preferably limited to about 3.0 to 5.0 millimeters so that the tubes 8c and 10c are not going to obstruct the air flow paths inside the base portions 8b and 10b and the top portions 8a and 10a of the nasal sealing members 8 and 10, respectively, when the tubes 8c and 10c are partially compressed or pushed into the base portions 8b and 10b or the top portions 8a and 10a. In at least one embodiment, there are no tubes 8c and 10c between the top portions 8a and 10a and the corresponding base portions 8b and 10b. As an alternative, the bottoms of the top portions 8a and 10a are directly connected to the tops of the corresponding base portions 8b and 10b, respectively. The second openings of the top portions 8a and 10a will be also the first openings of the corresponding base portions 8b and 10b.

It should be appreciated that the tubes 8c and 10c between the top portions 8a and 10a and the base portions 8b and 10b can be straight tubes without any corrugations or corrugated tubes that are not spirally corrugated as long as they are flexible and crush-resistant and provide a good flexibility. The tubes 8c and 10c may be angled to align the nasal sealing members 8 and 10, respectively, with the nasal air passageways in the nose. However, the corrugated configuration is preferred, because it not only provides a good flexibility but also helps retain moisture and reduce upper airway dryness.

The central tubular chamber 4 is a hollow cylindrical tube. In at least one embodiment, the central tubular chamber 4 is a flexible hollow cylindrical shape tube. The central tubular chamber 4 may be slightly curved such that the nasal sealing members 8 and 10 can be aligned with the nasal passages of the nose. It should be appreciated that the central tubular chamber 4 can be made in any other suitable shapes. In at least one embodiment, the central tubular chamber 4 is corrugated, flexible, crush-resistant, lightweight, and/or semi-transparent or transparent. The central tubular chamber 4 may be shaped in a way in which it fits the user's mustache area. It is placed beneath the user's nose and above the user's upper lip. The central tubular chamber 4 is built at a size that is large enough so that it can allow delivering gases to the nasal sealing members 8 and 10 during inhalation and discharging the exhaled gases from the nasal sealing members 8 and 10 during exhalation without significant resistance. The central tubular chamber 4 does not interfere with any manipulations in the mouth such as endotracheal intubation in conscious or unconscious patients.

Figure 3:
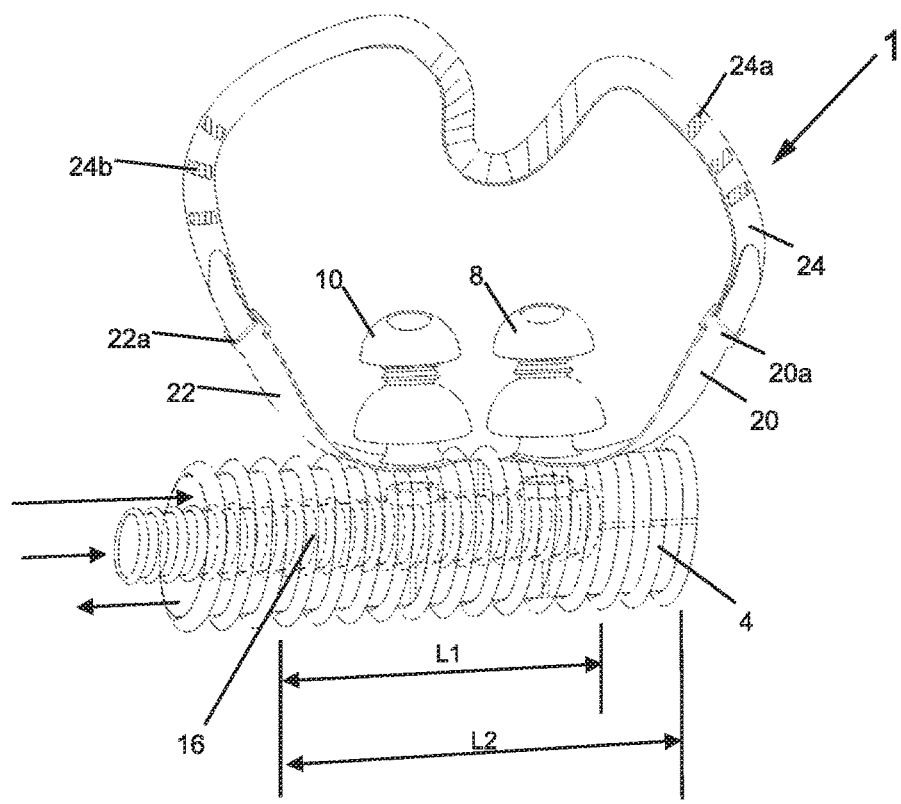
FIG. 3 shows a perspective view of part of the nasal breathing apparatus of FIG. 1.

For description purpose, the part of the wall of the central tubular chamber 4 facing the openings of the nostrils, the part facing a foot (not shown) of the standing person 100 wearing the apparatus 1, the part facing the face, and the part that is opposite to the face, are called top wall, bottom wall, back wall, and front wall, respectively (FIGS. 1, 2A, and 3). The top wall of the central tubular chamber 4 is connected to the bottoms of the base portions 10b and 8b of the nasal sealing members 10 and 8 by short tubes 10e and 8e. The short tubes 10e and 8e, respectively, have a first end that is also the second opening of the corresponding base portions 10b and 8b and a second end that is also an opening of the top wall of the central tubular chamber 4. The length of the short tubes 10e and 8e is limited and about 2.0 to 3.0 millimeters. In at least one embodiment, there are no short tubes 10e and 8e between the bottoms of the base portions 10b and 8b and the top wall of the central tubular chamber 4. The bottoms of the base portions 8b and 10b are directly attached to the top wall of the central tubular chamber 4 with the second openings in the centers of the bottoms of the base portions 8b and 10b, respectively. The second openings of the base portions 8b and 10b are directly connected to the corresponding openings of the top wall of the central tubular chamber 4. The inner diameter of the short tubes 10e and 8e is equal to or 10.0 to 20.0 percent larger than the inner diameter of the first openings of the base portions 10b and 8b, respectively. A larger short tube for short tubes 10e and 8e in diameter will help form a positive pressure within the mushroom-shaped base portions 10b and 8b, respectively, from the incoming gas flow and maintain the shape of the base portions 10b and 8b, respectively. The top wall of the central tubular chamber 4 may be slightly thickened and thicker than the other part of the central tubular chamber 4 to increase the strength and maintain the stability. In at least one embodiment, the nasal sealing members 8 and 10 only have the top portions 8a and 10a without the base portions 8b and 10b. The tubes 8c and 10c, in at least one embodiment of the nasal sealing members 8 and 10 (without base portions 8b and 10b and without short tubes 8e and 10e) are directly connected to the top wall of the central tubular chamber 4. In at least one embodiment, the nasal sealing members 8 and 10 only have the base portions 8b and 10b without the top portions 8a and 10a and without the tubes 8c and 10c. The base portions 8b and 10b, in such an embodiment, will seal the openings of the corresponding nostrils without forming an airtight seal inside the nostrils.

There is a side strap 20 on a left side and a side strap 22 on a right side of the top wall of the central tubular chamber 4 (FIGS. 1, 2A, and 3). The left and the right side straps 20 and 22 can be made integrally with the top wall of the central tubular chamber 4 or made separately from the central tubular chamber 4. The side straps 20 and 22 are laterally extended from the short tubes 8e and 10e, respectively. A portion of the side straps 20 and 22 is attached or fixed to the top wall of the central tubular chamber 4 to provide necessary strength for securing the central tubular chamber 4 in place. In at least one embodiment, the side straps 20 and 22 are made separately from the central tubular chamber 4 and formed as a single strap which has two holes on its middle part (not shown) that allows the short tubes 8e and 10e to just pass through. The side straps 20 and 22 are positioned between the bottoms of the base portions 8b and 10b and the top wall of the central tubular chamber 4, respectively. In at least one embodiment, the side straps 20 and 22 are angled upward (toward the nose) and create an angle of forty-five to sixty degrees between the nose and the side straps 20 and 22, respectively. The side straps 20 and 22 are also angled backward (toward the face) and create an angle of forty-five to sixty degrees between the face and the side straps 20 and 22, respectively. The length of the side straps 20 and 22 is preferably about three to five centimeters and the width about 1.0 to 2.0 centimeters. The width of the side straps 20 and 22 is preferably equal to or slightly larger than the outer diameter of the bottoms of the base portions 8b and 10b of the nasal sealing members 8 and 10 such that the side straps 20 and 22 can completely cover the bottoms of the base portions 8b and 10b of the nasal sealing members 8 and 10. The thickness of the side straps 20 and 22 is preferably about 1.0 to 2.0 millimeters so that the side straps 20 and 22 can fit in the spaces between the bottoms of the base portions 8*b* and 10*b* and the top wall of the central tubular chamber 4, respectively. The side straps 20 and 22 are made from soft tear resistant materials, such as silicone or the like. The surfaces of the side straps 20 and 22 that contact the nose and the face may be coated with a thin layer of silicone gels, soft thermoplastic elastomers, or the like to increase softness and reduce irritation to the skin. Each end of the side straps 20 and 22 is enlarged relative to the width of the side straps 20 and 22. The enlarged end has a slot, 20*a* for 20, and 22*a* for 22, for the attachment of a head strap 24. The side of the head strap 24 that contacts the face is smooth and soft. The other side of the head strap 24 is full of soft fuzzy loop fasteners and has three to five separate hook fastener pads, such as pad 24*a* and 24*b*, near each end of the head strap 24. The ends of the head strap 24 are passed through the slots 20*a* and 22*a* of the side straps 20 and 22, respectively, and looped back on themselves to hold the ends in place. The head strap 24 is placed around the back of a patient's head and above the ears to secure the central tubular chamber 4. The head strap 24 or a part of the head strap 24 is made from suitable elastic materials and is expandable so that the head strap 24 is extendable. When the head strap 24 is tightened, the side straps 20 and 22 will push or lift the bottoms of the base portions 8*b* and 10*b* of the nasal sealing members 8 and 10 toward the nose and will apply a net upward force on the patient's nose. The side straps 20 and 22 also apply a net backward force on the patient's face. The tension of the head strap 24 can be adjusted to provide the necessary upward and backward forces and produce adequate comfortable seals inside the nostrils and the outer of the nostrils. When positive pressure ventilation is needed, the head strap 24 is tightened so that the side straps 20 and 22 will be pulled upward against the bottoms of the base portions 8*b* and 10*b*, to seal the openings of the nostrils. The base portions 8*b* and 10*b* of the nasal sealing members 8 and 10 may be partially compressed and will form a sealing interface between the outer surfaces of the base portions 8*b* and 10*b* of the nasal sealing members 8 and 10, respectively, and the inner and the outer edges of the nostrils. When positive pressure ventilation is not needed, the head strap 24 can be left loose for just holding the central tubular chamber 4 in place and for delivering gases without applying excessive pressure on the nose. As an alternative, the side straps 20 and 22 may have buttons, lugs, anchors, attachment points, or the likes at or near their end edges for the attachment of a head strap 24 or the like to the side straps 20 and 22 to hold the central tubular chamber 4 in position against the patient's nose and the face. A breathing tube strap 30 is looped around the breathing tube 6 at a place that is close to the right end of the central tubular chamber 4 and the right side end of the head strap 24 for holding the breathing tube 6 away from the mouth and preventing the breathing tube 6 to pull the central tubular chamber 4 away from the face. The width of the breathing tube strap 30 is about 5 to 10 millimeters. As an alternative, one end of the breathing tube strap 30 is looped around the breathing tube 6 at a place that is close to the right end of the central tubular chamber 4 to hold the end on itself and the other end is affixed on the right side end of the head strap 24 or looped around the right side end of the head strap 24 to hold the other end on itself. As an alternative, a pair of attachment pads (not shown) are provided to support the breathing tube 6. One adhesive pad having a portion of a hook and loop fastener is attached to the breathing tube 6. Another adhesive pad having the other portion of a hook and loop fastener is attached to the face or to the right side of the head strap 24. The breathing tube 6 will be secured to the face or to the right side of the head strap 24 by putting the two attachment pads together. It should be appreciated that the nasal breathing apparatus 1 can be maintained in position on the face by any other suitable means without departing from the scope of the disclosed concept.

The back wall of the central tubular chamber 4, i.e., the part of the central tubular chamber 4 that sits on the face, can be curved and shaped in a way that fits a patient's mustache area. The outer surface of the back wall is soft and may be coated with a thin layer of silicone gels or the like. In at least one embodiment, the front wall of the central tubular chamber 4 can be also curved and shaped in a way that fits a patient's mustache area. This will increase flexibility and patient comfort when the patient wears the device in a reverse direction, i.e., the first nasal sealing member 8 being in the right nostril, the second nasal sealing member 10 in the left nostril, and the breathing tube 6 on the left side of the central tubular chamber 4.

The central tubular chamber 4 has a first end (a left side end) 4*c* and a second end (a right side end) 4*d* opposite to the first end 4*c*. The length L2 (the distance between the left side end 4*c* and the right side end 4*d*) of the central tubular chamber 4 is generally about three to six centimeters and is preferably at least 10.0 to 20.0 millimeters wider than the width of the nose of an adult. The central tubular chamber 4 is preferably formed in a corrugated configuration. The corrugated configuration provides more flexibility and help maintain the shape and integrity of the central tubular chamber 4 even though the central tubular chamber 4 is thin-walled and has a large inner diameter. The corrugated configuration also may help retain moisture and temperature and reduce airway dryness. The inner diameter of the central tubular chamber 4 is about 10.0 to 22.0 millimeters throughout its length L2 for an adult. The central tubular chamber 4 will be made in a size that allows the central tubular chamber 4 to be placed between the nose and the upper lip of the mouth and not to cover the mouth. In at least one embodiment, the top wall of the central tubular chamber 4 is made substantially flat so that the central tubular chamber 4 may be easier to fit the space between the nose and the upper lip of the mouth and the side straps 20 and 22 can be attached to a larger area of the top wall of the central tubular chamber 4. The left side end 4*c* of the central tubular chamber 4 is a closed end with a flat side wall or a curved or semi-cylindrical side wall. The right side end 4*d* of the central tubular chamber 4 is an open end and connected to the breathing tube 6. In at least one embodiment, the central tubular chamber 4 is made integral with the breathing tube 6 so that there are no connection elements between the central tubular chamber 4 and the breathing tube 6. There are also no exhaust or vent holes on the central tubular chamber 4, in at least one embodiment, so that there will be no air leaking from the central tubular chamber 4 itself during inhalation and exhalation. As an alternative, the right side end 4*d* of the central tubular chamber 4 is a closed end and while the left side end 4*c* of the central tubular chamber 4 is an open end and connected to the breathing tube 6. In at least one embodiment, the right side end 4*d* of the central tubular chamber 4 is an open end which is connected to the breathing tube 6 while the left side end 4*c* of the central tubular chamber 4 is also an open end which is configured so that the left side end 4*c* of the central tubular chamber 4 is blocked by a detachable cap or plug (not shown). The cap or the plug can be detached or removed from the left side end 4*c* of the central tubular chamber 4 for facilitating the intake of ambient air during inhalation and the discharge of the exhaled gases during exhalation and reducing the airflow resistance during spontaneous respiration when the device is used for delivering gases. The cap or the plug can be reattached back to the left side end 4c of the central tubular chamber 4 if needed.

The breathing tube 6, i.e., an outer tube, is corrugated, thin-walled, soft, flexible, crush-resistant, lightweight, and/or semi-transparent or transparent. The corrugated configuration of the breathing tube 6 will not only provide a good flexibility and prevent collapse, but also help retain moisture and heat and reduce airway dryness. The breathing tube 6 has a first end 6a and a second end 6b opposite to the first end 6a. The first end 6a of the breathing tube 6 is also the right side end 4d of the central tubular chamber 4. Since the breathing tube 6 and the central tubular chamber 4 are integrally formed as a single piece (the central tubular chamber 4 and the breathing tube 6 are actually a single tube) and there are no connection elements such as connectors, between them, the first end 6a of the breathing tube 6 and the right side end 4d of the central tubular chamber 4 are at the same position and their connecting point is indicated as 6a and 4d, which are at the same, or substantially the same location in FIG. 2A. The breathing tube 6 is configured to laterally extend from the right side end 4d of the central tubular chamber 4 and to curve downward at a position above the right corner of the mouth with the aid of the breathing tube strap 30 or the like such that the breathing tube 6 will not hang over or cover the mouth. In at least one embodiment, the breathing tube 6 is not corrugated. The inner diameter of the breathing tube 6 is about 10.0 to 22.0 millimeters for an adult and may be equal to, smaller than, or larger than the inner diameter of the central tubular chamber 4. The thickness of the wall of the breathing tube 6 and the central tubular chamber 4 is about 0.2 to 1.0 millimeters. The second end 6b of the breathing tube 6 is fixed to a first open end of the coupler 12. The length of the breathing tube 6 is preferably about 20.0 to 40.0 centimeters so that the nasal breathing device or apparatus 1 will be lightweight and the coupler 12 will not contact the face when the patient is put in any position. Since the coupler 12 is placed far away from the ears, the noise level from the exhaust gases will be significantly reduced. The length of the breathing tube 6 also can be extended by attaching a vent tube 3 (FIG. 2B) to the outlet 12f of the coupler 12 if needed. The vent tube 3 is preferably a corrugated flexible tube or a corrugate extendable flexible tube. One connector 3a of the vent tube 3 will be connected to the outlet 12f of the coupler 12 and the other connector 3b of the vent tube 3 will be placed away from the patient's face. The vent tube 3 will be thin-walled, lightweight, flexible, extendable, contractible, and crush-resistant. The vent tube 3 may have a same, a larger, or a smaller internal diameter as the breathing tube 6 and may have a reasonable length (e.g., 0.5 to 2 meters) so that the connector 3b of the vent tube 3 can be placed at a remote location from the ears and the noise level from the exhaust gases is further reduced or even becomes nonperceptible. The vent tube 3 also can be connected to a vacuum to facilitate the removal of the exhaust gases. In at least one embodiment, the breathing tube 6 is a reinforced tubing with a metal wire coil being embedded in the wall of the breathing tube 6 to increase the flexibility and prevent collapse. In at least one embodiment, the length of the breathing tube 6 will be more than 20.0 to 40.0 centimeters and is preferably 1.0 to 2.0 meters so that the outlet 12f of the coupler 12 can be located at a remote distance from the face.

The inner central tube 16 is positioned inside the central tubular chamber 4 at a position that is preferably more nearer to the bottom wall of the central tubular chamber 4 than to the top wall of the central tubular chamber 4. The inner central tube 16 has a first end (a left side end) 16g, a second end (a right side end) 16h opposite to the first end, a top wall (facing the openings of the nostrils), a bottom wall (facing a foot (not shown) of the standing person 100 wearing the apparatus 1), a back wall (facing the face), and a front wall (opposite to the face), defining a second chamber of the central tubular chamber 4. The space surrounding the inner central tube 16 (outside of the inner central tube 16) defines a first chamber of the central tubular chamber 4. The inner central tube 16 can be a corrugated tube or a straight tube with a few corrugations on the middle part or a straight tube without any corrugations. In at least one embodiment, the top wall of the inner central tube 16 may be made substantially flat. It should be appreciated that the inner central tube 16 can be made in any other suitable shapes without departing from the scope of the disclosed concept. The length L1, shown in FIG. 2A, of the inner central tube 16 may be equal to or slightly shorter than the length L2 of the central tubular chamber 4 shown in FIG. 2A. The inner diameter of the inner central tube 16 is preferably about one third to half of the inner diameter of the central tubular chamber 4. The inner central tube 16 and the delivery tube 14 may be colored. The inner central tube 16 can be attached or fixed to the bottom wall, the top wall, the back wall, and/or the front wall of the central tubular chamber 4 via a few support rods or the like such as 16c, 16d, and 16f (however, the support rods for the front wall and the back wall are not shown), so that the inner central tube 16 will not move within the central tubular chamber 4. The size of the support rods 16c, 16d, and 16f is limited (e.g., 1.0 to 2.0 millimeters in diameter) so that they will not block the airflow in the central tubular chamber 4. As an alternative, a part or the whole of the bottom wall of the inner central tube 16 can be directly affixed to the bottom wall of the central tubular chamber 4. The first end 16g of the inner central tube 16 is a closed end and is attached the inner wall of the left side end 4c of the central tubular chamber 4 via at least one support rod 16e or directly molded to the wall of the left side end 4c of the central tubular chamber 4. There are two holes or two ports 16a and 16b on the top wall of the inner central tube 16. Each of the holes or ports 16a and 16b is axially aligned with the corresponding openings of the top wall of the central tubular chamber 4 so that the delivered gases from the inner central tube 16 will be directed toward the nasal sealing members 10 and 8. The edges of the holes or ports 16a and 16b is preferably protruded or raised from the top wall of the inner central tube 16. The protruded or raised edges will help direct air flow from the inner central tube 16 toward the corresponding nasal sealing members 10 and 8 and not toward the breathing tube 6, so that the gases from the inner central tube will be delivered to the nasal sealing members 10 and 8 and not to the breathing tube 6. The height or the length of the raised or protruded edges is about 1.0 to 3.0 millimeters and configured in a way that the raised or protruded edges will not obstruct air flow from the base portions 10b and 8b of the nasal sealing members 10 and 8, respectively. In at least one embodiment, the height or length of the raised or protruded edges will be more than 1.0 to 3.0 millimeters and formed as prongs (not shown) toward the corresponding openings of the top wall of the central tubular chamber 4. The prongs should be built in a size that will not obstruct airflow from the nasal sealing members 10 and 8. The holes or ports 16a and 16b should be made as big as possible and the inner diameter of each hole or port 16a or 16b is preferably equal to the inner diameter of the inner central tube 16. In at least one embodiment, the edges of the holes or ports 16a and 16b are not protruded or raised from the top wall of the inner central tube 16.

The delivery tube 14 is an inner tube that is positioned inside the breathing tube 6, defining an inner lumen of the breathing tube 6 in communication with the inner central tube 16. The space surrounding the delivery tube 14 defines an outer lumen of the breathing tube 6. The delivery tube 14 has a first end 14a and a second end 14b opposite to the first end 14a. The inner central tube 16 is made integral with the delivery tube 14 such that there will be no connection elements such as connectors, between the inner central tube 16 and the delivery tube 14 (the inner central tube 16 and the delivery tube 14 are integrally formed into a single tube). The first end 14a of the delivery tube 14 is also the second end 16h of the inner central tube 16. The first end 14a of the delivery tube 14 and the second end 16h of the inner central tube 16 are at a same position and their connecting point is indicated as 16h and 14a, which may be at the same or substantially the same location in FIG. 2A. In at least one embodiment, both the delivery tube 14 and the breathing tube 6 are flexible, expandable, and contractible. They can be extended or contracted along their lengths.

The second end 14b of the delivery tube 14 is fixed to a curved tube 12d that is positioned inside the coupler 12. The curved tube 12d exits on the proximal part of the coupler 12 at a smooth right angle or at an angle of 30.0 to 45.0 degrees and is formed as a gas supplying port 12a. The gas supplying port 12a and the curved tube 12d are made from the same material as the coupler 12. The gas supplying port 12a may have a same inner diameter or a different inner diameter as the curved tube 12d shown in FIGS. 1 and 2A. The length of the gas supplying port 12a is about 10.0 to 15.0 millimeters. The gas supplying port 12a is shaped in a way that it can be connected to a gas supplying tubing 15 as shown in FIG. 1 from a gas supplying source. In at least one embodiment, a cap (not shown) is provided and attached to the gas supplying port 12a via an elastic ring or the like and can block the gas supplying port 12a when it is not needed. The cap (not shown) is made from soft materials, such as silicone or the like. In at least one embodiment, the second end 14b of the delivery tube 14 is directly connected to the gas supplying port 12a without a curved tube 12d. In at least one embodiment, the delivery tube 14 directly exits on the proximal part of the coupler 12 and continues as a gas supplying tubing. The length of the gas supplying tubing from the exit point on the coupler 12 is about 7.0 to 8.0 feet. The gas supplying tubing is flexible, lightweight, and crush-resistant. The end of the gas supplying tubing is shaped in a way that it can be attached to a gas supplying source. In at least one embodiment, the gas supplying port 12a is configured in a way that a standard anesthesia circuit adaptor can be connected to the gas supplying port 12a. The gas flow direction from the delivery tube 14 is changed at the two holes or ports 16a and 16b of the inner central tube 16 and the gas flow is redirected toward the nasal sealing members 10 and 8. There will be no or minimal air jetting effects on the nasal airway because the combined inner diameter of the holes or ports 16a and 16b of the inner central tube 16 is larger than the inner diameter of the delivery tube 14 and the velocity of the gas flow will be significantly decreased. Such arrangements may increase the patient comfort by reducing jet effects and noise from high velocity gas flow. The central tubular chamber 4, the inner central tube 16, the breathing tube 6, and the delivery tube 14 are made from silicone, polypropylene, or the like. They are highly flexible, thin-walled, lightweight, crush-resistant, and/or semi-transparent or transparent. The inner diameter of the delivery tube 14 is preferably about one third to half of the inner diameter of the breathing tube 6 so that the expired gases can be discharged through the first chamber of the central tubular chamber 4 (inside the central tubular chamber 4 and outside the inner central tube 16) and the outer lumen of the breathing tube 6 (inside the breathing tube 6 and outside the delivery tube 14) without significant resistance. The thickness of the wall of the delivery tube 14 and the inner central tube 16 is about 0.2 to 1.0 millimeters.

The coupler 12 has a first open end, a second open end, one gas sampling port 12b, one gas supplying port 12a, and a half ring or a D-ring 12c. The coupler 12 may be indented on its both open ends so that the first open end of the coupler 12 is connected to the second end 6b of the breathing tube 6 and the second open end is an outlet 12f which is configured to fit a standard anesthesia circuit adaptor. The outer or the inner diameter of the outlet 12f may be 22.0 or 15.0 millimeters and the length may be 10.0 to 15.0 millimeters. The coupler 12 is generally equal to or larger than the breathing tube 6 in diameter, depending on the size of the breathing tube 6. The length of the coupler 12 may vary and is about 40.0 to 50.0 millimeters generally. The coupler 12 is made from polypropylene, silicone, polysulfone, polycarbonate, polyvinyl chloride, or the like and is rigid or semi-rigid. The coupler 12 should be lightweight, crush-resistant, and/or semi-transparent or transparent. The coupler 12 will be positioned near the neck above the shoulder or in front of the chest when one is wearing the nasal breathing device 1.

The gas sampling port 12b is preferably positioned on the opposite side of the gas supplying port 12a. The gas sampling port 12b may have an inner diameter of 2 to 5 millimeters and a length of about 10 millimeters. The gas sampling port 12b may be a male Luer with a female Luer cap or a female Luer with a male Luer cap and can be connected to a gas sampling tubing 17 as shown in FIG. 1 for gas sampling. As an alternative, the gas sampling port 12b can be pre-attached or pre-formed as a gas sampling tubing. The female Luer cap or the male Luer cap is preferably made from soft materials, such as silicone or the like. The female Luer cap or the male Luer cap can be attached to the port via an elastic ring or the like (not shown). As an alternative, the gas sampling port 12b can be located at any position between the coupler 12 and the first end of the breathing tube 6. In at least one embodiment, there is no gas sampling port on the coupler 12. An adaptor with a gas sampling port (not shown) may be attached to the outlet 12f of the coupler 12 for gas sampling.

It will be appreciated by one having ordinary skill in the art that the lengths and the sizes of the breathing tube 6, the delivery tube 14, the inner central tube 16, and the central tubular chamber 4 can be varied without departing from the scope of the disclosed concept. The ratio of the inner diameter of the delivery tube 14 and the inner diameter of the breathing tube 6 may be varied as long as the outer lumen of the breathing tube 6 is large enough for discharging the exhaled gases without significant resistance and the delivery tube 14 is also large enough for delivering high flow of gases.

The half ring 12c or the like is preferably located on the same side of the gas sampling port 12b. As an alternative, there may be a locking ring (not shown) on the coupler 12 or the distal part of the breathing tube 6. One end of a neck strap 40 in FIG. 1 or the like is attached to the half ring 12c or the like on the coupler 12 and the other end of the neck strap 40 or the like can have a badge clip 42 or the like that can be used to position the coupler 12 and the breathing tube 6 on the patient's neck collar 102 or the clothes and increase the stability of the device or apparatus 1 and wearing comfort. In at least one embodiment, there is no half ring 12c, locking ring or the like on the coupler 12. A strap with a self-adhesive hook and loop (not shown) is used to position the coupler 12 and the breathing tube 6. One end of the strap is attached to the coupler 12 or the distal part of the breathing tube 6 via a self-adhesive hook and loop while the other end can have a badge clip, similar or identical to 42, or the like that can be used to position the coupler 12 and the breathing tube 6 on the patient's neck collar 102 or the clothes. The length of the neck strap 40 can be adjusted to support the coupler 12 and the breathing tube 6 so that the coupler 12 (including the gas sampling tubing 17 and the gas supplying tubing 15) and the breathing tube 6 (the delivery tube 14) will not pull the central tubular chamber 4 away from the face resulting from their weight. It is appreciated that the coupler 12 and the breathing tube 6 can be supported by any other suitable means.

Figure 2B:
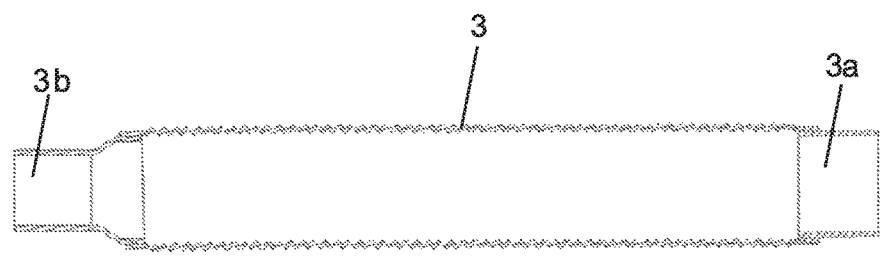
FIG. 2B shows a simplified diagram of a longitudinal section of a vent tube.
Figure 2C:
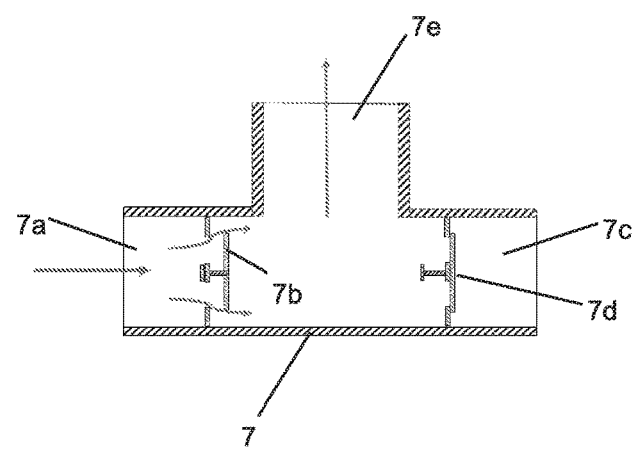
FIG. 2C shows a simplified diagram of a cross-sectional view of a non-rebreathing tee adaptor.

In at least one embodiment, a non-rebreathing tee adaptor 7 is provided (FIG. 2C). The non-rebreathing tee adaptor 7 has one inspiratory port 7a that has a one-way inspiratory valve 7b, one expiratory port 7c that has a one-way expiratory valve 7d, and one connection port 7e that can be connected to the outlet 12f of the coupler 12. During inhalation, the one-way inspiratory valve 7b opens and the one-way expiratory valve 7d closes as shown in FIG. 2C, which only allows ambient air from the one-way inspiratory port 7a to enter the non-rebreathing tee adaptor 7, the coupler 12, and the outer lumen of the breathing tube 6. During exhalation, the one-way inspiratory valve 7b closes and the one-way expiratory valve 7d opens, which only allows the exhaust gases from the outer lumen of the breathing tube 6 and the coupler 12 be discharged through the expiratory port 7c. Both the inspiratory port 7a and the expiratory port 7c are configured so that they can fit a standard anesthesia circuit adaptor. The one-way expiratory valve 7d, in at least one embodiment, can be configured in a way that it can provide variable resistance to expiratory airflow during exhalation. An adjustable (positive end expiratory pressure) valve (not shown) can be attached to the expiratory port 7c if needed. When the apparatus 1 is used for CPAP therapy, much lower air flow rates will be needed to attain the same therapeutic pressures compared to the existing patient interfaces. As an alternative, the non-rebreathing tee adaptor 7 can made integral with or preformed or attached to the coupler 12. Both the one-way inspiratory valve 7b and the one-way expiratory valve 7d may have any other suitable configurations other than the configuration shown in FIG. 2C and may be formed from any suitable soft and compliant materials so that they will make little or no noise when they close and open during use.

The nasal sealing members 8 and 10, the central tubular chamber 4, the inner central tube 16, the breathing tube 6, and the delivery tube 14 may be integrally formed in one-piece or may be made separately and molded together. There typically will be no joints or connectors near the face and the nose. The delivery tube 14 runs coaxially inside the breathing tube 6. The breathing tube 6 is connected to the central tubular chamber 4 either leftwardly or rightwardly and the outlet 12f of the coupler 12 is positioned far away from the face. Thus, the nasal interface of one or more embodiments of the present invention will be compact and lightweight and will offer optimal comfort for the patient.

The presence of the central tubular chamber 4 and the breathing tube 6 will increase anatomic dead space and the risk of rebreathing because the exhaled gases are washed out through the outer lumen of the breathing tube 6 during expiration and may be inhaled during next inspiration. However, the anatomic dead space will be only slightly increased with the nasal interface of the present invention. For a breathing tube 6 with a length of 40.0 centimeters and an inner diameter of 20.0 millimeters, the combined volume of the breathing tube 6 and the central tubular chamber 4 is about 140.0 cubic milliliters. The added anatomic dead space (the volume of the outer lumen of the breathing tube 6 and the first chamber of the central tubular chamber 4) is about 100.0 cubic milliliters (after deducting the volume of the delivery tube and the inner central tube). The amount of rebreathing will be dependent on the fresh gas flow and the patient's breathing pattern. When fresh gas is not provided, the amount of rebreathing may be significant (about 20% of the exhaled gases being inhaled during next inhalation). The rebreathing will become more significant if the patient breathes in a rapid and shallow pattern. This is because a greater portion of tidal volume will be from the added anatomic dead space when tidal volume is significantly decreased. Thus, adequate fresh gas flow must be provided to decrease or prevent rebreathing when the patient's respirations are rapid and shallow.

The coaxial arrangement of the breathing tube 6 and the delivery tube 14 is similar to a Bain breathing circuit or a single limb coaxial breathing circuit. When the nasal breathing apparatus 1 of one or more embodiments of the present invention is used for delivering gases in a spontaneously breathing patient, fresh gas flows through the delivery tube 14 which is located within the breathing tube 6. During expiration, fresh gas flow pushes exhaled gas down the outer lumen of the breathing tube 6 (outside of the delivery tube 14) and exhaled gas will be flushed out of the breathing tube 6. The exhaled gas in the outer lumen of the breathing tube 6 surrounds and warms the fresh gas in the inner lumen of the breathing tube 6 (inside the delivery tube), thus reducing heat loss and maintaining humidity of the inspired gases. The outer lumen of the breathing tube 6 will be filled with fresh gas from the delivery tube 14 for next inspiration. During inspiration, the patient inspires fresh gas from the delivery tube 14, the outer lumen of the breathing tube 6, and ambient air. Thus, no rebreathing will occur when adequate fresh gas flow is provided. For an adult, a fresh gas flow of equal to or more than 2 lpm will be required to prevent rebreathing during spontaneous respiration. When the device or apparatus 1 is used for CPAP, there will be no rebreathing even with a vent tube 3 (a length of 1.0 to 2.0 meters) being attached to the outlet 12f of the coupler 12 because the flow rate from a flow generator is generally more than 30 lpm. During mechanical ventilation, the effects of the added anatomic dead space from the breathing tube 6 and the central tubular chamber 4 can be easily overcome by increasing minute ventilation or by increasing fresh gas flow.

For delivering oxygen, the gas supplying port 12a in FIG. 2A, is connected to a gas supplying tubing 15 and oxygen is delivered to the nasal airway from the gas supplying port 12a and the delivery tube 14 via the inner central tube 16 and the nasal sealing members 8 and 10 and the exhaled gases are discharged to ambient from the nasal sealing members 8 and 10 through the first chamber of the central tubular chamber 4 and the outer lumen of the breathing tube 6 and sampled from the gas sampling port 12b. The first chamber of the central tubular chamber 4 and the outer lumen of the breathing tube 6 act as an oxygen reservoir during exhalation. The delivered gases are directed to the nasal airway and there will be no gases leaking into the ambient air through the nostrils. Since the volume of the first chamber of the central tubular chamber 4 and the outer lumen of the breathing tube 6 is small and washed with fresh gas, the rebreathing of the exhaled gases will not occur or will be not significant. During inspiration, the patient inspires fresh gas from the delivery tube 14, the first chamber of the central tubular chamber 4, the outer lumen of the breathing tube 6, and ambient air. During expiration, fresh gas washes the expired gas out of the first chamber of the central tubular chamber 4 and the outer lumen of the breathing tube 6 and fills them with fresh gas for the next inspiration. For those patients who are not comfortable with the nasal sealing members 8 and 10 being placed inside the nostrils, the top portions 8a and 10a of the nasal sealing members 8 and 10, respectively, can be gently placed just outside of the nostrils or only one of the nasal sealing members 8 and 10 is placed inside one of the nostrils with the other nostril being left open. The top portions 8a and 10a of the nasal sealing members 8 and 10 still can form physical sealing interfaces around the openings of the nostrils when low flow or high flow of oxygen is delivered because of their unique configuration. After the patient is adequately sedated, the top portions 8a and 10a of both nasal sealing members 8 and 10, respectively, can be placed inside the nostrils if needed.

For nasal insufflation, the gas supplying port 12a can be connected to one gas supplying source via a regular connector or two gas supplying sources via a Y-type connector. The total flow rate can easily reach up to twenty-five to sixty liters per minute, depending upon the gas supplying sources being used. Since there are no gases being wasted and all delivered gases are directed to the nasal airway via the nasal sealing members 8 and 10, a much lower flow rate will be needed to achieve nasal insufflation. Unlike regular nasal cannulas, high flow nasal cannulas, or other nasal interfaces, high velocity gas from the delivery tube 14 does not directly flow toward the nasal airway. The airflow is redirected from the holes or ports 16a and 16b of the inner central tube 16 to the nasal airway through the nasal sealing members 10 and 8 and the velocity of airflow is significantly decreased because the combined inner diameter of the openings of the nasal sealing members 8 and 10 is larger than the inner diameter of the delivery tube 14. Thus, there will be no or minimal jetting effects on the nasal airway. The patient will be more comfortable with the nasal interface of the present invention. For a short period of time, humidification and heating are not necessary. The corrugated configuration and the tube-in-tube configuration (coaxial configuration) will help retain the moisture and temperature. For a prolonged period of time, a humidified and heated gas can be delivered with the commercially readily available heated humidifiers. It will be very useful for preoxygenation during general anesthesia and emergency endotracheal intubation. It will increase the patient's comfort and safety and decrease the incidents of hypoxemia during intubation. It also can be used as a rescue measure to decrease the chance for intubation or reintubation. The excessive gases escape from the outer lumen of the breathing tube 6 and the mouth, which decreases the anatomical dead spaces by flushing the nasal cavities, oropharynx, and oral cavity during the exhalation. It is less wasteful and significantly increases the inspired oxygen concentration during inhalation.

To attain CPAP, the gas supplying port 12a can be connected to a gas supplying tubing or a gas supplying conduit of a CPAP machine. The head strap 24 can be tightened so that the mushroom-shaped base portions 8b and 10b of the nasal sealing members 8 and 10, respectively, will seal the openings of the corresponding nostrils. The gases flow into the nasal airway through the nasal sealing members 8 and 10 and the exhaled gases are discharged into the outer lumen of the breathing tube 6 via the nasal sealing members 8 and 10. The high velocity of the incoming gas flow does not have a direct impact on the nostrils and will not cause significant discomfort. The treatment pressure can be monitored through the gas sampling port 12b. If used in a hospital setting, a CPAP machine may be not needed because a regular wall flow meter can deliver a gas flow up to 30 lpm and attain a moderate CPAP level (8 to 10 $cmH_2O$). If needed, a non-rebreathing tee adaptor 7 can be attached to the outlet 12a of the coupler 12 and an adjustable PEEP (positive end expiratory pressure) valve can be attached to the exhalation port 7c of the non-rebreathing tee adaptor 7. The oxygen flow rate and/or the adjustable PEEP valve can be adjusted to achieve a desired level of CPAP. The presence of the outer lumen of the breathing tube 6 allows ambient air to enter the nasal sealing members 8 and 10 during inhalation and the delivered gases from the holes or ports 16a and 16b also entrain gases from the first chamber of the central tubular chamber 4 because of the Venturi effect. This will reduce the flow rate that is required for attaining a desired CPAP level and will reduce the work of breathing. The reduced flow rate not only will reduce power consumption of a flow generator but also will cause less noise. Unlike other existing nasal interfaces (the exhaust or vent ports for exhalation at or near the nose), the nasal breathing apparatus 1 of one or more embodiments of the present invention has no exhaust or vent ports for exhalation at or near the face and the exhaust or the vent port (the outlet 12f of the coupler 12) is placed far away from the patient's face. If needed, one connector 3a of the vent tube 3 can be attached to the outlet 12f of the coupler 12 and another connector 3b of the vent tube 3 can be placed at a remote distance from the face. This will significantly decrease the noise from the exhaust gases. The nasal breathing apparatus 1 of one or more embodiments of the present invention is lightweight and compact and does not need a heavy support headgear or similar devices. The unique dual seal configuration will help maintain a constant seal even at maximum therapy pressures and the nasal interface of the present invention will have less gas leaking. It will be more comfortable for a patient to wear and will allow the patient to change head position freely. This will significantly increase patient comfort and compliance.

For nasal positive pressure ventilation, the outlet 12f of the coupler 12 can be connected to an anesthesia circuit or a resuscitator bag with the gas supplying port 12a and the gas sampling port 12b being blocked or connected to the gas supplying tubing 15 and the gas sampling tubing 17, respectively. The head strap 24 will be tightened and the base portions 8b and 10b of the nasal sealing members 8 and 10, respectively, will be firmly against the openings of the corresponding nostrils. The mushroom-shaped base portions 8b and 10b will seal the openings of the corresponding nostrils. There is no need, in at least one embodiment, for an additional face mask or nasal mask. One can easily switch between high flow oxygen therapy and positive pressure ventilation without changing the patient interface. To facilitate the nasal ventilation, the mouth can be closed by a simple maneuver (chin lift) and the airway can be opened by a jaw thrust maneuver. It is easier to perform these maneuvers with the nasal breathing apparatus 1 of one or more embodiments of the present invention than with a face or nasal mask. For those patients with upper airway obstruction, a nasopharyngeal airway can be placed to relieve airway obstruction. The top portion 8a or 10a of one of the nasal sealing members 8 or 10, respectively, can be directly inserted into the nasopharyngeal airway or can be connected to the nasopharyngeal airway by a short tube or the like (not shown). Positive pressure ventilation can be achieved more easily and effectively.

Figure 4:
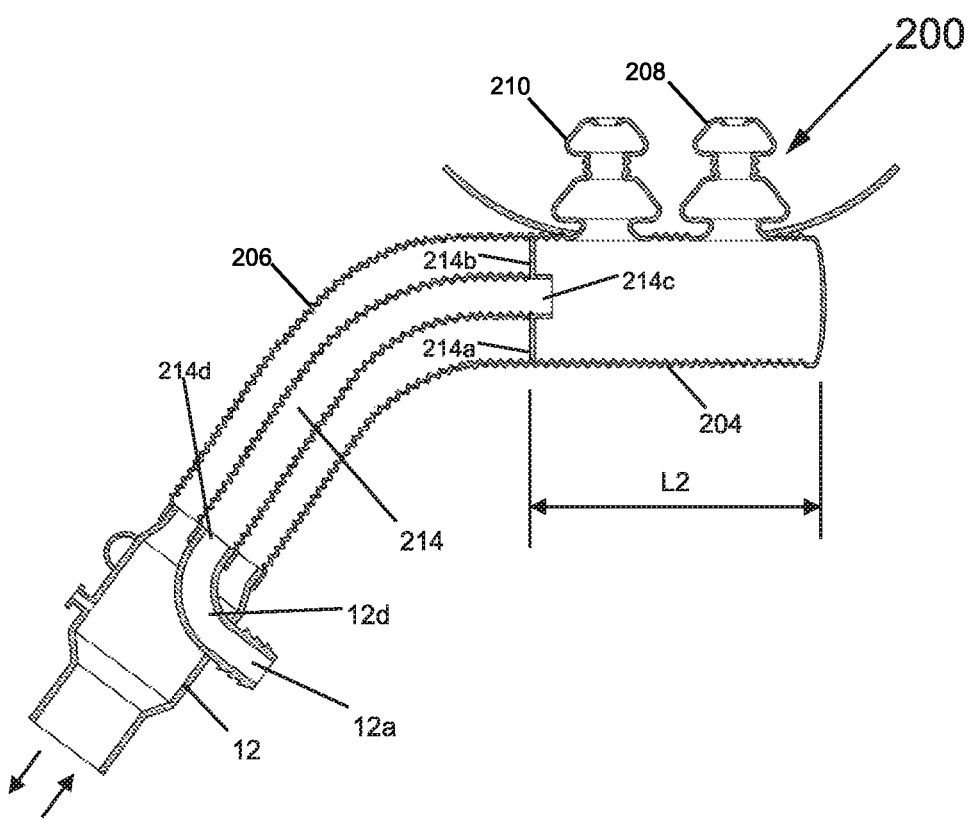
FIG. 4 shows a simplified diagram of a front cross-sectional view of part of second nasal breathing apparatus, somewhat different from that in FIG. 1, in accordance with another embodiment of the present invention.

In another embodiment as shown in FIG. 4, there is no inner central tube and a first end 214c of a delivery tube 214 is preferably located within the central tubular chamber 204 at a position near the right side end of the central tubular chamber 204. FIG. 4 shows an apparatus 200 which may be the same as the part of the apparatus shown in FIG. 2A and used with FIG. 1, except as will be described. The part of the delivery tube 214 near the first end 214c of the delivery tube 214 is fixed to the inner wall of the central tubular chamber 204 via a few support rods 214a and 214b or the like or the bottom wall of the part of the delivery tube 214 near the first end 214c is directly attached or fixed to the bottom wall of the central tubular chamber 204, so that the first end 214c of the delivery tube 214 will not move. The delivery tube 214 has a second end 214d that is fixed to a first open end of a curved tube 12d that is positioned within the coupler 12. The nasal breathing apparatus of FIG. 4 has all functions as the nasal breathing apparatuses of FIGS. 1 and 2A.

In various embodiments of the nasal breathing apparatuses of FIGS. 1 and 2A, both the inner central tube 16 and the delivery tube 14 are made bigger in size and have an inner diameter about half to two thirds of that of the central tubular chamber 4 and the breathing tube 6, respectively. In these embodiments, the outer lumen of the breathing tube 6 is used for delivering gases from the outlet 12f of the coupler 12 to the first chamber of the central tubular chamber 4 and the nasal sealing members 8 and 10. The inner lumen of the breathing tube 6 is used for conducting gases from and to the second chamber of the central tubular chamber 4 and the nasal sealing members 8 and 10. In various embodiments of the nasal breathing apparatuses of FIG. 4, the delivery tube 214 is made bigger in size and has an inner diameter about half to two thirds of that of the breathing tube 206 so that the outer lumen of the breathing tube 206 is used for delivering gases to the central tubular chamber 204 and the nasal sealing members 208 and 210 and the inner lumen of the breathing tube 206 is used for conducting gases from and to the central tubular chamber 204 and the nasal sealing members 208 and 210. The configuration of the breathing tube and the delivery tube in these various embodiments is similar to a Lack breathing system. These various embodiments have all functions as the nasal breathing apparatuses of FIGS. 1 and 2A.

FIG. 5A shows a simplified diagram of a front cross-sectional view of part of a nasal interface or apparatus 300 according to another embodiment of the present invention. The apparatus 300 may be the same as shown in FIGS. 1 and 2A, except as will be described. Basically, the apparatus 300 has or functions with the nasal sealing members 8 and 10, the side straps 20 and 22, the head strap 24, the breathing tube strap 30, the non-rebreathing tee adaptor 7, and the vent tube 3 as previously described in the first embodiment of the present invention with reference to FIGS. 1 to 3.

The apparatus 300 has a central tubular chamber 304 and a breathing tube (an outer tube) 306 that is laterally connected to a right side end of the central tubular chamber 304. The central tubular chamber 304 and the breathing tube 306 may be the same as shown in FIGS. 1 and 2A, except will be described. An inner septum or partition 304b segregates the central tubular chamber 304 into a first chamber 304a (equivalent to the first chamber of the central tubular chamber 4 of FIGS. 1 and 2A) and a second chamber 316 (equivalent to the second chamber of the central tubular chamber 4 of FIGS. 1 and 2A), and the breathing tube 306 into a breathing lumen 306c (equivalent to the outer lumen of the breathing tube 6 of FIGS. 1 and 2A) and a delivery lumen 314 (equivalent to the inner lumen of the breathing tube 6 of FIGS. 1 and 2A) (FIGS. 5A, 5C, and 5D). The first chamber 304a and the second chamber 316 of the central tubular chamber 304 may have a same length L3. The cross-sectional area of the second chamber 316 and the cross-sectional area of the delivery lumen 314 is about one third to half of that of the central tubular chamber 304 and that of the breathing tube 306, respectively, such that the patient can breathe in and out through the nasal interface without significant resistance and high-flow gases can be administered. The inner septum 304b has a first end that terminates at a left side wall 304c of the central tubular chamber 304 and an opposite end that terminates at one end of a coupler septum 312d. The second chamber 316 has two holes or ports 316a and 316b (similar or identical to 16a and 16b of FIG. 2A) which are located on a top wall of the second chamber 316 and aligned with the corresponding openings of a top wall of the central tubular chamber 304 for directing and delivering gases to the corresponding nasal sealing members 310 and 308 via the first chamber 304a. The top wall of the second chamber 316 is a part of the inner septum 304b, which is also a bottom wall of the first chamber 304a. The holes or ports 316a and 316b are configured as the same as described in the first embodiment of the present invention. The thickness of the inner septum 304b is about 0.2 to 1.0 millimeters. In at least one embodiment, the breathing tube 306 is flexible, corrugated, extendable, and contractible and the inner septum 304b is also corrugated so that the inner septum 304b and the breathing tube 306 can be contracted or extended along their lengths. The coupler septum 312d segregates the coupler 312 into a breathing passage 312h and a delivery passage 312g (FIGS. 5A and 5B). The delivery passage 312g has a first end that is in fluid communication with the delivery lumen 314 and a second end that is closed by a flat or curved wall 312i. The coupler septum 312d and the second end wall 312i of the delivery passage 312g may be made in a same material as the coupler 312 and may have a same thickness as the wall of the coupler 312. A gas supplying port 312a is connected to the delivery passage 312g and a gas sampling port 312b is connected to the breathing passage 312h. Both the gas supplying port 312a and the gas sampling port 312b are configured as the same as described in the first embodiment of the present invention. In at least one embodiment, the central tubular chamber 304 has no inner central tube as in FIG. 4 and is not segregated by an inner septum as shown for example in FIG. 6A. FIG. 6A has a coupler 412, which may be identical to coupler 312, and has a central tubular chamber 404 having no inner central tube as in FIG. 4. FIG. 6A shows apparatus 400 which may have nasal sealing members 408 and 410, breathing tube 406, breathing lumen 406c, delivery lumen 414, coupler 412, gas supplying port 412a, gas sampling port 412b, and outlet 414f. The central tubular chamber 404 has a length L4 which may be equal to the length L2 of the central tubular chamber 4 of FIG. 2A. The inner septum 404b extends axially starting from a right side end of the central tubular chamber 404 and segregates the breathing tube 406 into a breathing lumen 406c and a delivery lumen 414 (FIGS. 6A-D). The inner septum 404b terminates at one end of a coupler septum 412d. The coupler septum 412d segregates the coupler 412 into a breathing passage 412h and a delivery passage 412g (FIG. 6B). The cross-sectional area of the delivery lumen 414 is about one third to half of that of the breathing tube 406.

In various embodiments of the nasal breathing apparatuses of FIG. 5A, both the second chamber 316 of the central tubular chamber 304 and the delivery lumen 314 are made bigger in size and have a cross-sectional area about half to two thirds of that of the central tubular chamber 304 and the breathing tube 306, respectively. In various embodiments of the nasal breathing apparatuses of FIG. 6A, the delivery lumen 414 is made bigger in size and has a cross-sectional area about half to two thirds of that of the breathing tube 406. In these embodiments, the breathing lumen 306c or 406c will act as a delivery lumen and is used for delivering gases from the outlet 312f or 412f of the coupler 312 or 412 to the first chamber 304a of the central tubular chamber 304 or the central tubular chamber 404, and the nasal sealing members 308 and 310 or 408 and 410, respectively. The delivery lumen 314 or 414 will act as a breathing lumen and is used for conducting gases from and to the second chamber 316 of the central tubular chamber 304 or the central tubular chamber 404, and the nasal sealing members 308 and 310 or 408 and 410, respectively.

The nasal interfaces of the embodiments of FIG. 5A or 6A of the present invention have all functions as the nasal interfaces of the embodiments of FIGS. 1-4 of the present invention and have several additional advantages. Unlike coaxially arranged breathing tube and delivery tube in the nasal interfaces of embodiments of FIGS. 1-4, the breathing tube 306 or 406 is divided into a breathing lumen 306c or 406c and a delivery lumen 314 or 414 by an inner septum 304b or 404b, respectively. The central tubular chamber 304 is also divided into two segregated chambers 304a and 316 in an apparatus 300 of FIG. 5A. The weight of the nasal interfaces of the embodiments of FIG. 5A or 6A of the present invention will be significantly reduced. The central tubular chamber 304 or 404 and the breathing tube 306 or 406 also can be made significantly smaller in size compared to those of the nasal interfaces of the embodiments of FIGS. 1-4. Thus, the nasal interfaces of the embodiments of FIG. 5A or 6A will be more compact and lightweight and provide less bulk for the patient. It will greatly increase patient comfort and compliance. The double lumen configuration of the central tubular chamber 304 and the breathing tube 306 or 406 is similar to that of a single limb double lumen breathing circuit. When the nasal interface with apparatus 300 of FIG. 5A or 400 of FIG. 6A is used for delivering gases and administering CPAP, the gas supplying port 312a or 412a is connected to a gas supplying source via a supplying tubing, or a conduit. The fresh gas from the gas supplying port 312a or 412a enters the delivery passage 312g or 412g of the coupler 312 or 412 and travels along within the delivery lumen 314 or 414 to the second chamber 316 of the central tubular chambers 304 or the central tubular chamber 404, and the nasal sealing members 308 and 310 or 408 and 410, respectively. Since the direction of the gas flow from the delivery lumen 314 or 414 is changed, there will be no jet effects on the nasal passageways. The exhaled gas is discharged to the ambient through the outlet 312f or 412f of the coupler 312 or 412 via the nasal sealing members 308 and 310 or 408 and 410, the first chamber 304a of the central tubular chamber 304 or the central tubular chamber 404, and the breathing lumen 306c or 406c, respectively. The exhaled gas also can be sampled through the gas sampling port 312b or 412b, respectively. The fresh gas in the delivery lumen 314 or 414 is heated by the expired gas in the breathing lumen 306c or 406c, thus helping reduce heat loss and maintain humidity. If needed, a non-rebreathing tee adaptor 3 shown in FIG. 2C or a vent tube 3 shown in FIG. 2B can be attached to the outlet 312f or 412f of the coupler 312 or 412. When the nasal interface is used for NIV (non-invasive ventilation) or rescue breathing, an anesthesia circuit or a resuscitator bag is connected to the outlet 312f or 412f with the gas supplying port 312a or 412a and the gas sampling port 312b or 412b being blocked or connected to the gas supplying tubing and the gas sampling tubing, respectively. During spontaneous respiration, rebreathing will not occur with adequate fresh gas flow. During mechanical ventilation, the effects of the added anatomic dead space from the breathing lumen 306c or 406c can be easily reduced or overcome by increasing minute ventilation or by increasing fresh gas flow. The same breathing device can be used for delivering low flow or high flow of gases, monitoring $EtCO_2$ (partial pressure or maximal concentration of carbon dioxide at the end of an exhaled breath) and providing CPAP and positive pressure ventilation. No patient interface change is needed.

Figure 7:
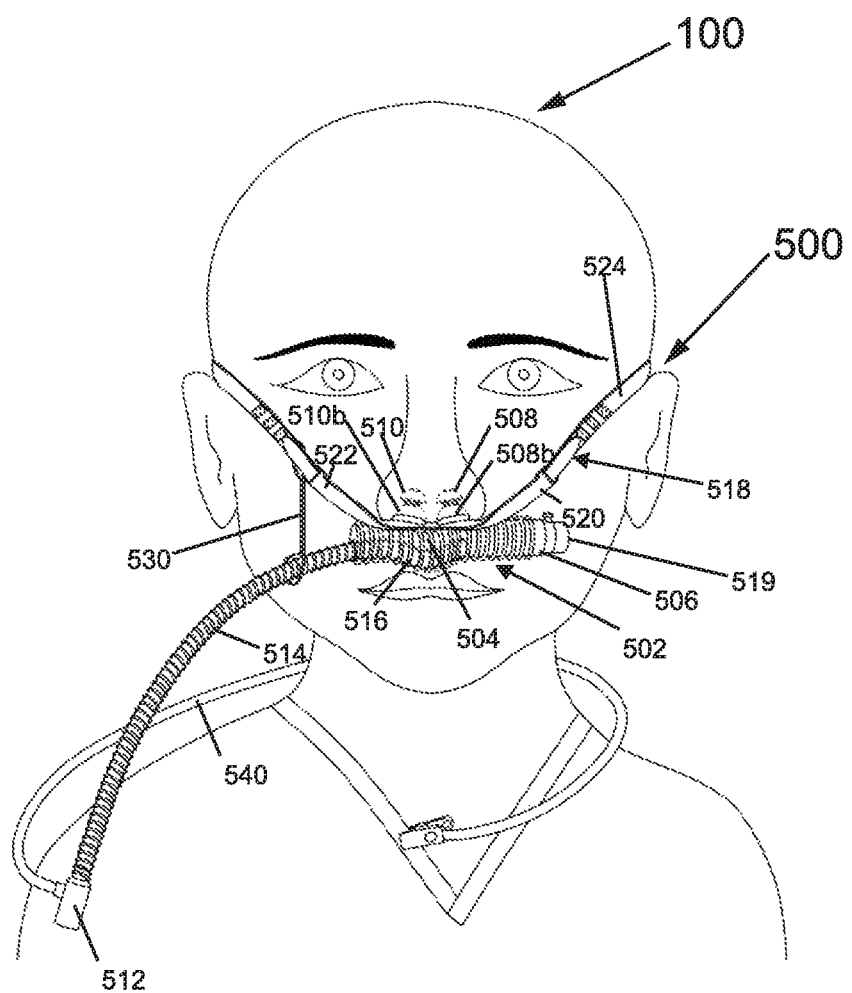
FIG. 7 shows a simplified diagram of a front view of a nasal breathing apparatus in accordance with another embodiment of the present invention being worn by a patient.
Figure 8:
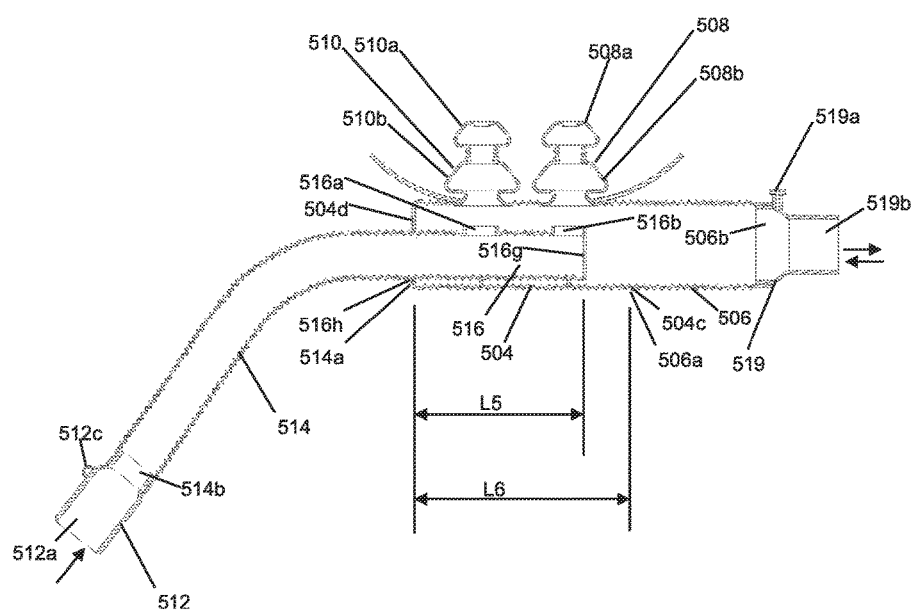
FIG. 8 shows a simplified diagram of a front cross-sectional view of part of the nasal breathing apparatus of FIG. 7.

With reference to FIG. 7, an apparatus 500 of another embodiment of the present invention is shown in which the patient or person 100 is wearing the apparatus 500. The apparatus 500 includes a main portion 502 and a head strap system 518. The apparatus 500 may be the same as apparatus 1 of FIGS. 1 and 2A, unless otherwise indicated as follows. FIG. 8 shows a simplified diagram of a front cross-sectional view of part of a nasal breathing apparatus 500 of FIG. 7. The main portion 502 of the apparatus 500 includes six main members: a first nasal sealing member 508, a second nasal sealing member 510, a central tubular chamber 504, an inner central tube 516, a delivery tube 514, and a breathing tube 506. Basically, the nasal sealing members 508 and 510 including top portions 508a and 510a and base portions 508b and 510b, the inner central tube 516, the central tubular chamber 504 and the side straps 520 and 522 have or share all the features and configurations of similarly numbered components described with reference to FIGS. 1 to 4, except as will be described.

The central tubular chamber 504 has a first end (a left side end) 504c and a second end (the right side end) 504d opposite to the first end 504c. The first end 504c of the central tubular chamber 504 is an open end and connected to a first end 506a of the breathing tube 506. The breathing tube 506 is made integral with the central tubular chamber 504 to form into a single tube and there are no connection elements such as connectors, between them. The first end 506a of the breathing tube 506 and the first end 504a of the central tubular chamber 504 are at a same position and their connecting point is indicated as 506a and 504c, which may be at the same or substantially the same location in FIG. 8. The breathing tube 506 is corrugated, soft, flexible, crush-resistant, lightweight, and/or semi-transparent or transparent. The corrugated configuration of the breathing tube 506 will not only provide a good flexibility and prevent collapse, but also help retain moisture and heat and reduce airway dryness. In at least one embodiment, the breathing tube 506 is not corrugated. In at least one embodiment, the breathing tube 506 is a flexible, extendable, and contractible tubing and can be extended if needed. The inner diameter of the breathing tube 506 is about 10 to 22 millimeters for an adult and may be equal to, or smaller or larger than the central tubular chamber 504. The thickness of the wall of the breathing tube 506 and the central tubular chamber 504 is about 0.2 to 1 millimeters. The breathing tube 506 may be attached to the left side strap 520 or the left side of the head strap 524 by any suitable means (e.g., a breathing tube strap 30 as described in the first embodiment of the present invention and shown in FIG. 1) to prevent the breathing tube 506 hanging down. A second end 506b of the breathing tube 506 is attached to a first connector 519. The length of the breathing tube 506 is preferably about five to ten centimeters so that the nasal breathing device or apparatus 500 will be lightweight and the connector 519 will not contact the face when the patient is put in any position. The length of the breathing tube 506 can be extended by attaching a vent tube 3 shown in FIG. 2B to the outlet 519b of the connector 519 if needed. In at least one embodiment, the breathing tube 506 is a reinforced tube with a metal wire coil being embedded inside the wall of the breathing tube 506. A reinforced breathing tube will increase the flexibility and prevent collapse. The outlet 519b of the connector 519 is configured so that it can fit a standard anesthesia circuit adaptor. The connector 519 may be made from polypropylene, silicone, polysulfone, polycarbonate, polyvinyl chloride, or the like. The connector 519 is lightweight, crush-resistant, and/or semi-transparent or transparent. The breathing tube 506 acts as a conduit for the passage of inhaled and exhaled gases and is used for discharging the exhaled gases from the central tubular chamber 504 and the nasal sealing members 508 and 510 during expiration, for conducting gases to the central tubular chamber 504 and the nasal sealing members 508 and 510 from ambient during inspiration, and for providing NIV.

The connector 519 may have a gas sampling port 519a which is preferably positioned on the upper portion of the connector 519 or the bottom portion or the front portion of the connector 519 so that the gas sampling port 519a will not contact the face. The gas sampling port 519a is configured as the same as described for the gas sampling port 12b in the first embodiment of the present invention and shown in FIGS. 1 and 2A. In at least one embodiment, there is no gas sampling port on the connector 519. An adaptor with a gas sampling port (not shown) may be attached to the outlet of the connector 519 for gas sampling if needed.

The inner central tube 516 has a first end (a left side end) 516g and a second end (a right side end) 516h opposite to the first end. The first end 516g of the inner central tube 516 is a closed end. The inner central tube 516 is positioned inside the central tubular chamber 504 at a location that is more nearer to the bottom wall of the central tubular chamber 504 than to the top wall of the central tubular chamber 504, defining a second chamber of the central tubular chamber 504. The inner central tube 516 can be a corrugated tube or a straight tube without any corrugations. The space surrounding the inner central tube 516 defines a first chamber of the central tubular chamber 504. The inner diameter of the inner central tube 516 is about one third to half of the inner diameter of the central tubular chamber 504 so that the air flow from the nasal sealing members 508 and 510 will not be obstructed. The inner central tube 516 has two holes or ports 516a and 516b on its top wall as shown in FIG. 8. The holes or ports 516a and 516b are configured as the same as described in the first embodiment of the present invention for directing and delivering the delivered gases from the inner central tube 516 to the nasal sealing members 510 and 508. The length L5 of the inner central tube 516 is generally shorter than or equal to the length L6 of the central tubular chamber 504.

Figure 9:
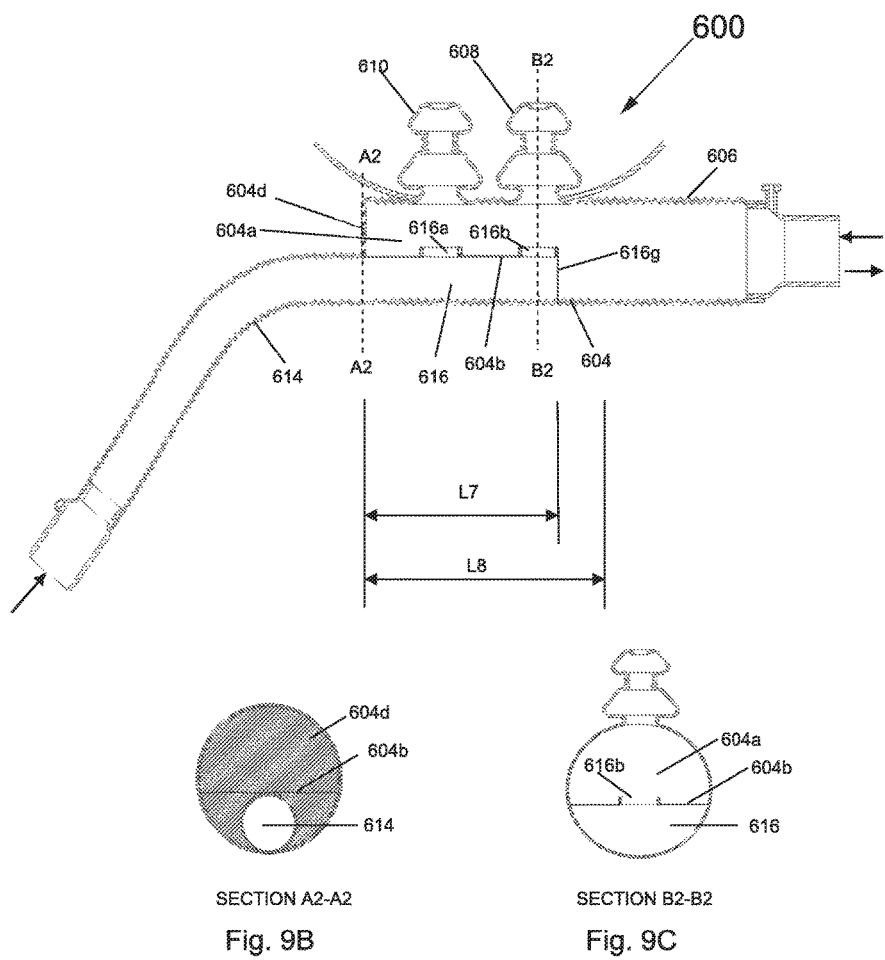
FIG. 9A shows a simplified diagram of a front cross-sectional view of part of the nasal breathing apparatus, somewhat different from that in FIG. 7, in accordance with another embodiment of the present invention.
FIG. 9B shows a cross-sectional view of the nasal breathing apparatus of FIG. 9A along a line A2-A2.
FIG. 9C shows a cross-sectional view of the nasal breathing apparatus of FIG. 9A along a line B2-B2.

In various embodiments, there is no inner central tube and central tubular chamber 604 is divided into a first chamber 604a (equivalent to a first chamber of the central tubular chamber 504 of FIGS. 7 and 8) and a second chamber 616 (equivalent to a second chamber of the central tubular chamber 504 of FIGS. 7 and 8) by an inner septum or partition 604b as shown in FIG. 9A for apparatus 600. FIG. 9A shows an apparatus 600 which may be the same as the part of the apparatus 500 shown in FIG. 8 and used with FIG. 7, except as will be described. The central tubular chamber 604 has a first end that is an open end and is connected to a breathing tube 606 and a second end that is a closed by a flat or curved wall 604d. The second chamber 616 has a first end which is closed by a side wall or septum 516g and a second end which is partially closed by the second side wall 604d of the central tubular chamber 604. The inner septum 604b extends axially from the second end wall 604d of the central tubular chamber 604 and terminates at the side wall 616g. The length L7 of the second chamber 616 may be shorter than or equal to the length L8 of the central tubular chamber 604. The delivery tube 614 is connected to the second chamber 616 of the central tubular chamber 604 at the second end wall 604d and in fluid communication with the second chamber 616 of the central tubular chamber 604 (FIG. 9B). The second chamber 616 has two holes or ports 616a and 616b (similar or identical to 516a and 516b of FIG. 8) which are located on a top wall of the second chamber 616 and aligned with the corresponding openings of the nasal sealing members 610 and 608 (FIGS. 9A and C). The top wall of the second chamber 616 is a part of the inner septum 604b, which is also a bottom wall of the first chamber 604a. The hole or ports 616a and 616b are configured as the same as described in the first embodiment of the present invention. The cross-sectional area of the second chamber 616 is about one third to half of that the central tubular chamber 604. The nasal interface of the embodiment of FIG. 9A of the present invention has all functions as the nasal interfaces of the embodiments of FIGS. 7-8 of the present invention, but it will be more compact and lightweight.

Figure 10:
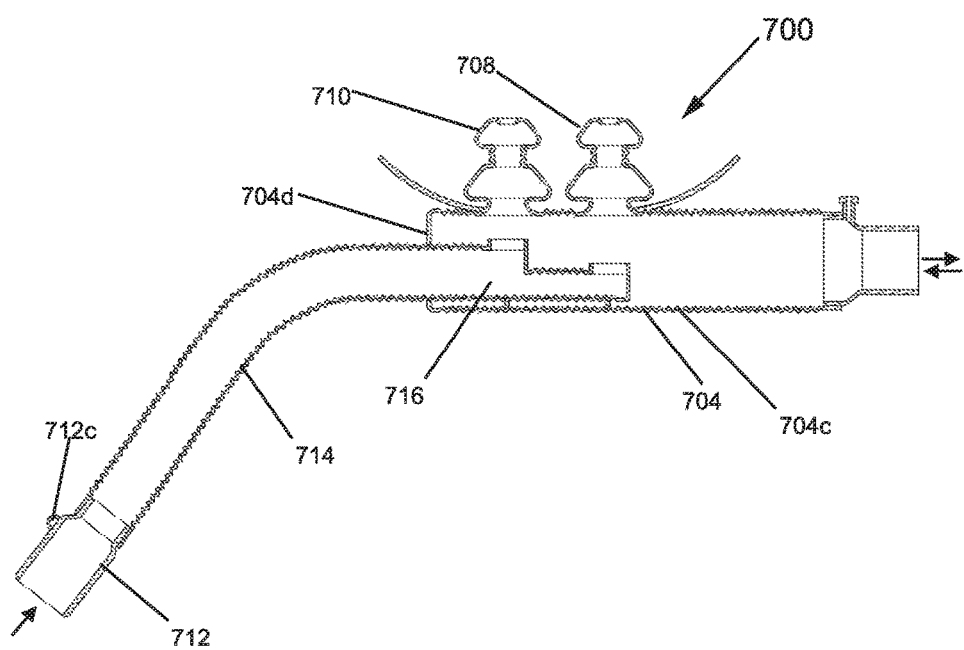
FIG. 10 shows a simplified diagram of a front cross-sectional view of part of the nasal breathing apparatus, somewhat different from that in FIG. 7, in accordance with another embodiment of the present invention.

In at least one embodiment, the inner central tube 516 may be replaced by a shorter inner center tube (not shown) and only has one hole or port on its top wall. The central tubular chamber will have more space available for conducting gases from or to the nasal sealing members than in FIG. 8 for the central tubular chamber 504. In at least another embodiment for an apparatus 700 shown in FIG. 10, the part of the inner central tube 716 near the first end 704c of a central tubular chamber 704 is made smaller in diameter than the part near the second end 704d of a central tubular chamber 704 so that there will be more space available for conducting gases from or to the nasal sealing members 708 and 710 (FIG. 10). The apparatus 700 may be similar or identical to what is disclosed in FIG. 8, except as specified. The apparatus 700 includes a connector 712 which has a D-ring 712c or a half ring on the top wall of the connector 712 near the second end of the delivery tube 714. The half ring or D-ring 712c is configured as the same as described in the first embodiment of the present invention.

The apparatus 500 of FIG. 7 includes a delivery tube 514 (614 in 600 of FIG. 9A and 714 in 700 of FIG. 10). The delivery tube 514 has a first end 514a and a second end 514b opposite to the first end 514a. The first end 514a of the delivery tube 514 is connected to the second end 516h of the inner central tube 516 at a location at the second end 504d of the central tubular chamber 504 as indicated in FIG. 8. The second end 504d of the central tubular chamber 504 is a closed end. The inner central tube 516 and the delivery tube 514 are formed integrally as a single tube. The connecting point of the first end 514a of the delivery tube 514 and the second end 516h of the inner central tube 516 is indicated as 514a and 516h, which may be at the same or substantially the same location in FIG. 8. The delivery tube 514 can be a corrugated flexible tube, an extendable and contractible corrugated flexible tube, or a tube without any corrugations. However, a corrugated configuration is preferable because it provides a good flexibility and prevents collapse. The delivery tube 514 may have a same size or a different size as the inner central tube 516, depending upon the size of the inner central tube 516. Generally, the inner diameter of the delivery tube 514 is about one third to half of that of the breathing tube 506. Both the breathing tube 506 and the delivery tube 514 are made from silicone, polypropylene, or the like. They are highly flexible, lightweight, crush-resistant, and/or semi-transparent or transparent. The second end 514b of the delivery tube 514 is connected a second connector 512 which is configured in a way that a gas supplying tubing or a hose or a standard anesthesia circuit can be attached. The length of the delivery tube 514 is about 20.0 to 40.0 centimeters so that the connector 512 can be placed near the neck or in front of the chest. There will be a delivery tube strap 530 to hold the delivery tube 514 away from the mouth and prevent the delivery tube 514 from pulling the central tubular chamber 504 away from the nose. The delivery tube strap 530 is configured as the same as described for the breathing tube strap 30 in the first embodiment of the present invention and shown in FIG. 1. The connector 512 has a D-ring 512c or a half ring on the top wall of the connector 512 near the second end of the delivery tube 514. The half ring or D-ring 512c is configured as the same as described in the first embodiment of the present invention. A strap 540 or the like can be attached to the half ring or D-ring 512c. The strap 540 can be adjusted to support the connector 512 and the delivery tube 514 so that the connector 512 including the gas supplying tubing and the delivery tube 514 will not pull the central tubular chamber 504 away from the face resulting from the weight of the connector 512, the delivery tube 514, and the gas supplying tubing.

Figure 11:
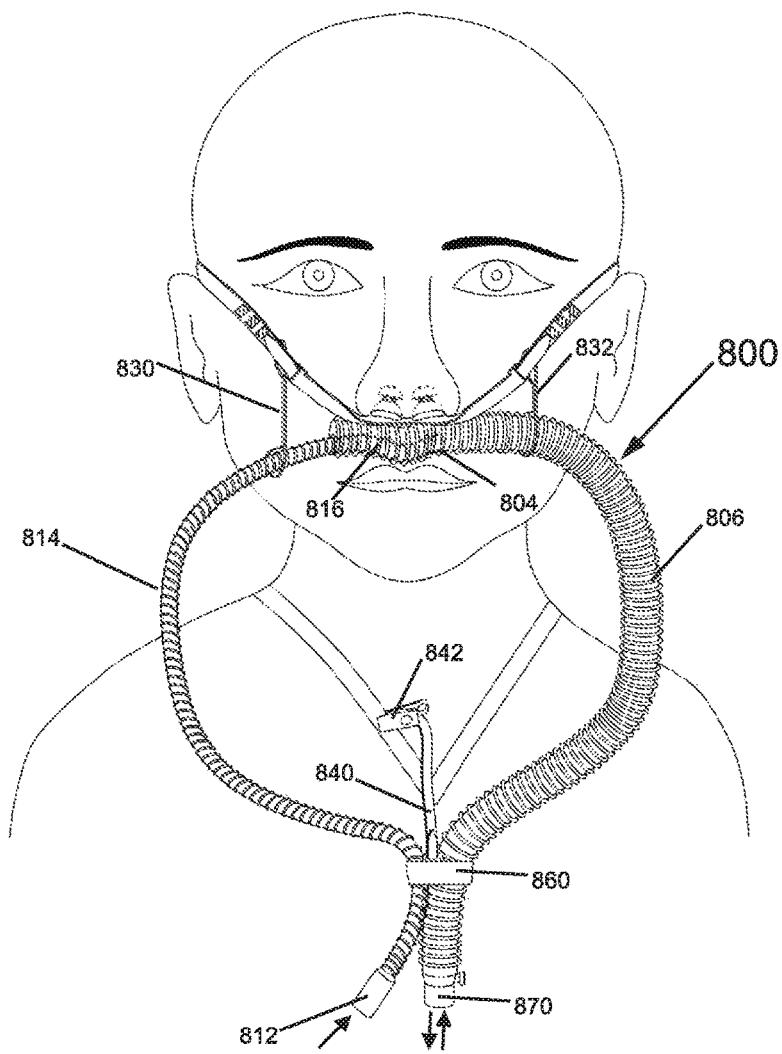
FIG. 11 shows a simplified diagram of a front view of a nasal breathing apparatus in accordance with another embodiment of the present invention being worn by a patient.

In at least one embodiment, as shown in FIG. 11, a breathing tube 806 is provided which has the same length as a delivery tube 814 as part of an apparatus 800. The breathing tube 806 and the delivery tube 814 are held together with a self-adhesive band 860 or the like being placed near their second ends as shown in FIG. 11. A strap 840 has one end which is attached to the self-adhesive band 860 or the like and another end which is attached to a badge clip 842 or the like. The badge clip 842 or the like is attached to the clothes of the user for supporting the breathing tube 806 and the delivery tube 814. There will be a delivery tube strap 830 and a breathing tube strap 832 to hold the delivery tube 814 and the breathing tube 806 respectively, away from the mouth. The breathing tube strap 832 and the delivery tube strap 830 are configured as the same as described for the breathing tube strap 30 in the first embodiment of the present invention and shown in FIG. 1. Since the outlet of a connector 870 of the breathing tube 806 is placed away from the face, there will be less noise during use. The apparatus 800 includes inner central tube 816 (identical to 516 in FIGS. 7 and 8) and central tubular chamber 804 (identical to 504 in FIGS. 7 and 8), and connector 812 (identical to 512 in FIGS. 7 and 8). In at least one embodiment, the connector 812 may be incorporated with the connector 870 to form a single coupler (not shown).

It will be appreciated by one having ordinary skill in the art that the lengths and the sizes of the breathing tube, the delivery tube, the inner central tube or the first chamber and second chamber of the central tubular chamber, and the central tubular chamber in the apparatuses 500, 600, 700, and 800 of FIGS. 7 to 11 can be varied without departing from the scope of the disclosed concept. The ratio of the cross-sectional area of the second chamber and the cross-sectional area of the first chamber of the central tubular chamber in the apparatus 600 of FIG. 9A and the ratio of the inner diameter of the inner central tube and the inner diameter of the central tubular chamber in the apparatuses 500, 700, and 800 of FIGS. 7, 8, 10, and 11 may be varied as long as the first chamber of the central tubular chamber is large enough for discharging the exhaled gases without significant resistance and the second chamber of the central tubular chamber is also large enough for delivering high flow of gases.

The nasal interfaces of the embodiment of FIGS. 7 to 11 of the present invention has all functions as the nasal interfaces of the embodiment of FIGS. 1 and 2 of the present invention. For description purpose, only the functions of the apparatus 500 of the embodiment of FIGS. 7 and 8 is explained. When the nasal interface is used for delivering gases and CPAP, the connector 512 is connected to a gas supplying source via a tubing, or a conduit. The fresh gas from the connector 512 is delivered to the nasal airway through the delivery tube 514, the inner central tube 516, the first chamber of the central tubular chamber 504, and the nasal sealing members 508 and 510. The exhaled gas is discharged to ambient through the nasal sealing members 508 and 510, the first chamber of the central tubular chamber 504, the breathing tube 506, and the outlet 519b of the connector 519 and sampled through the gas sampling port 519a. If needed, a non-rebreathing tee adaptor 7 shown in FIG. 2C or a vent tube 3 shown in FIG. 2B can be attached to the outlet 519b of the connector 519. When the nasal interface of apparatus 500 is used for NIV or rescue breathing, an anesthesia circuit or a resuscitator bag can be connected to the outlet 519b of the connector 519 of the breathing tube 506 with the outlet 512a of the connector 512 being blocked or connected to the gas supplying tubing. Since the breathing tube 506 is short, rebreathing will not occur with adequate fresh gas flow during spontaneous respiration. During mechanical ventilation, the effects of the added anatomic dead space from the breathing tube 506 can be easily reduced or overcome by increasing minute ventilation or by increasing fresh gas flow. Since the delivery tube 514 is not positioned inside the breathing tube 506, the breathing tube 506 will have more space available for discharging the exhaled gases and there will be less resistance during expiration. The patient will feel more comfortable because airflow is not impeded during inspiration and expiration. As an alternative, the outlet 519b of the connector 519 of the breathing tube 506 is blocked and the outlet 512a of the connector 512 is connected to an anesthesia circuit or a resuscitator bag for NIV. The same breathing device can be used for delivering low flow or high flow of gases, monitoring end tidal $CO_2$, and providing CPAP and positive pressure ventilation. No patient interface change is needed.

Figure 12:
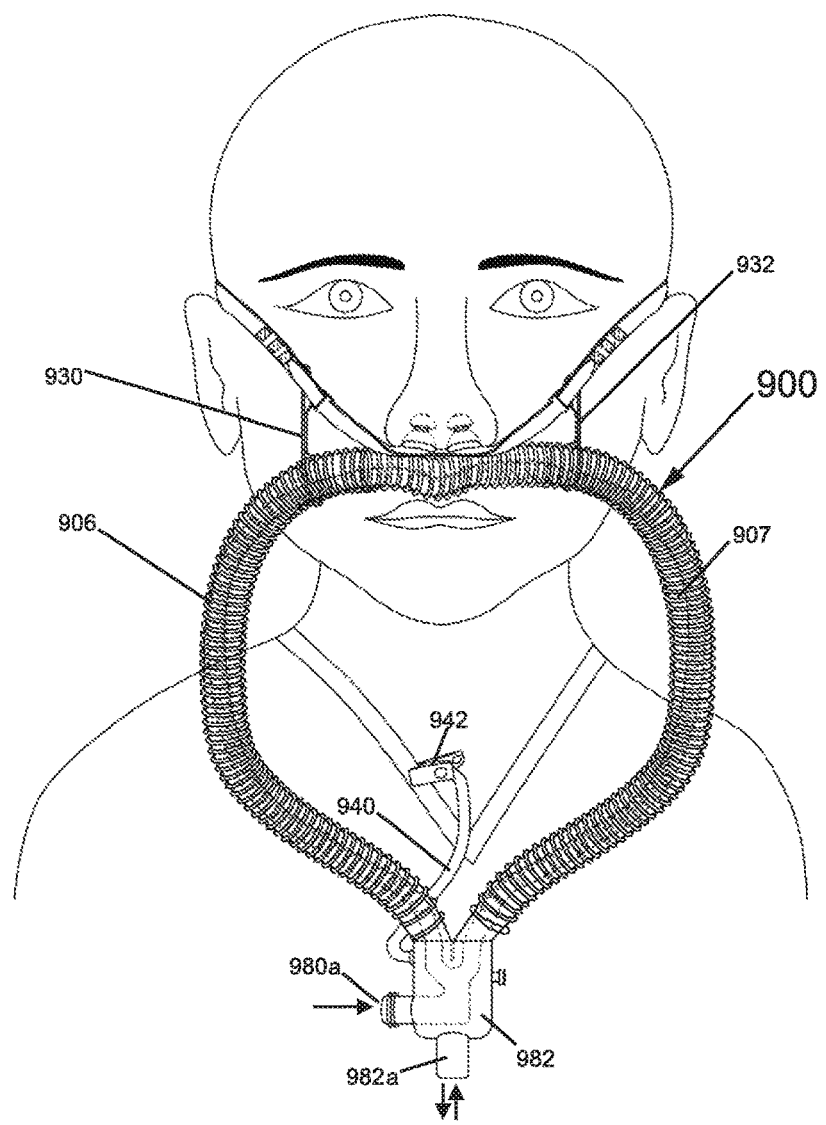
FIG. 12 shows a simplified diagram of a front view of a nasal breathing apparatus in accordance with another embodiment of the present invention being worn by a patient.
Figure 13:
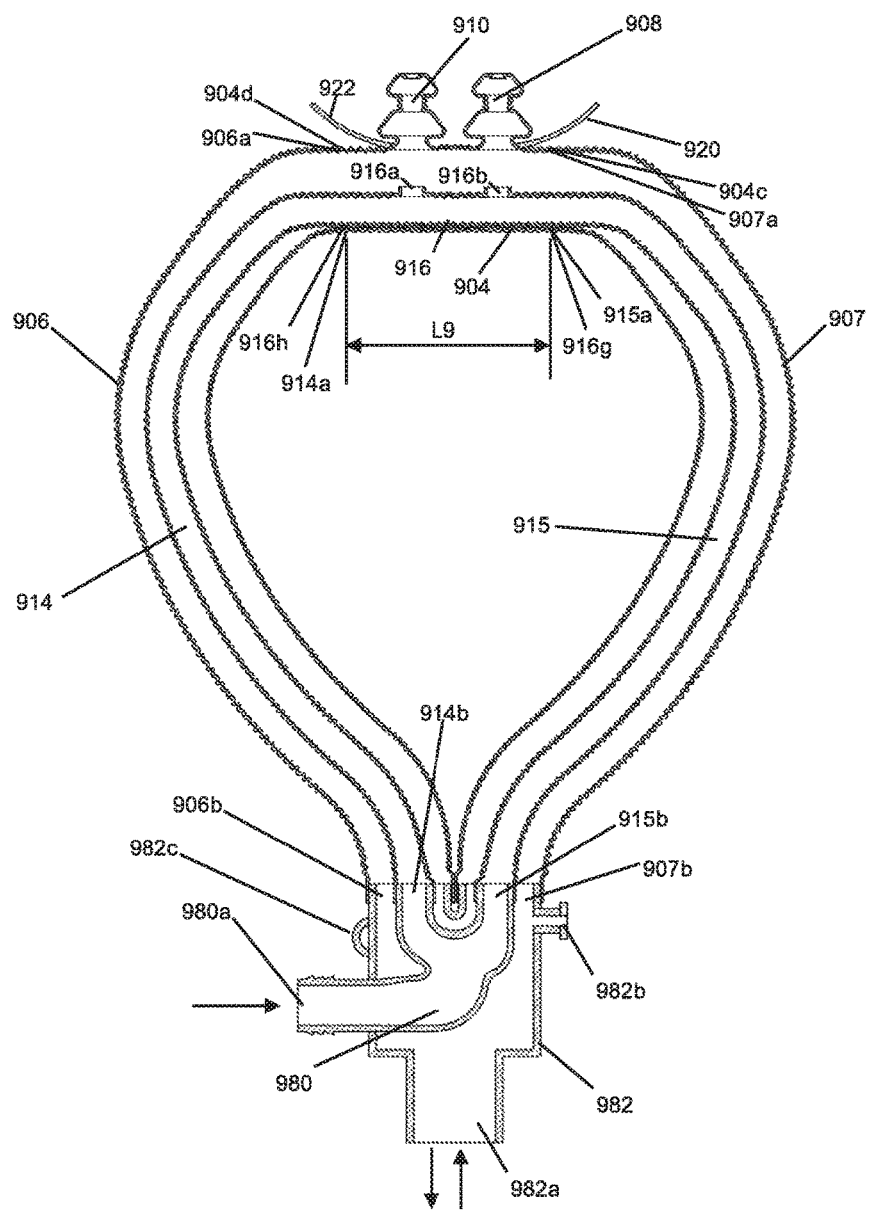
FIG. 13 shows a simplified diagram of a front cross-sectional view of part of the nasal breathing apparatus of FIG. 12.

With reference to FIG. 12, an apparatus 900 of another embodiment of the present invention is shown in which a patient or person is wearing the apparatus 900. FIG. 13 shows a simplified diagram of a front cross-sectional view of part of a nasal interface or apparatus 900 of FIG. 12. A main portion of the apparatus 900 includes a first nasal sealing member 908, a second nasal sealing member 910, a central tubular chamber 904, an inner tubular chamber 916, a pair of delivery tubes 914 and 915, and a pair of breathing tubes 906 and 907. Basically, the nasal sealing members 908 and 910, the central tubular chamber 904, the inner central tube 916, the breathing tubes 906 and 907, the delivery tubes 914 and 915, and the side straps 920 and 922 have or share all the features and configurations of those as described in the embodiment of the present invention with reference to FIGS. 1 to 2A, except as will be described.

The central tubular chamber 904 has a first end (a left side end) 904c and a second end 904d (a right side end) opposite to the first end 904c. The inner diameter of the central tubular chamber 904 is about 10.0 to 22.0 millimeters for an adult. A first end 907a of a left breathing tube (a left outer tube) 907 is laterally connected to the first end 904c of the central tubular chamber 904 and a first end 906a of a right breathing tube (a right outer tube) 906 is laterally connected to the second end 904d of the central tubular chamber 904. The left and the right breathing tubes 907 and 906 are made integral with the central tubular chamber 904 and formed into a single tube so that there are no connection elements such as connectors, between the breathing tubes 907 and 906 and the central tubular chamber 904. The first end 904c of the central tubular chamber 904 is also the first end 907a of the left breathing tube 907. The connecting point of the central tubular chamber 904 with the breathing tube 907 is indicated as 904c and 907a, which may be located at the same or substantially the same location in FIG. 13. The second end 904d of the central tubular chamber 904 is also the first end 906a of the right breathing tube 906. The connecting point of the central tubular chamber 904 with the right breathing tube 906 is indicated as 904d and 906a, which may be located at the same or substantially the same location in FIG. 13. The left and the right breathing tubes 907 and 906 are preferably a corrugated tube. The corrugated configuration of the breathing tubes 907 and 906 will not only provide a good flexibility and prevent collapse, but also help retain moisture and heat and reduce airway dryness. In at least one embodiment, the breathing tubes 907 and 906 are not corrugated. A second end 907b of the left breathing tube 907 and a second end 906b of the right breathing tube 906 are connected to a Y-shaped coupler 982. The length of either of the breathing tubes 907 and 906 is about 20.0 to 40.0 centimeters so that the Y-shaped coupler 982 can be positioned in front of the chest. The Y-shaped coupler 982 has an outlet 982a that is configured to fit a standard anesthesia circuit adaptor. The inner diameter of the breathing tube 907 or 906 is about 10.0 to 22.0 millimeters for an adult and may be equal to, smaller than, or larger than the inner diameter of the central tubular chamber 904. The breathing tubes 907 and 906 act as conduits and are used for discharging the exhaled gases from the central tubular chamber 904 and the nasal sealing members 908 and 910 during expiration, for conducting gases to the central tubular chamber 904 and the nasal sealing members 908 and 910 from ambient during inspiration, and for proving NIV. There will be a right breathing tube strap 930 and a left breathing tube strap 932 to hold the right breathing tube 906 and the left breathing tube 907 respectively, away from the mouth. The left and the right breathing straps 932 and 930 are configured as the same as described for the breathing tube strap 30 in the first embodiment of the present invention and shown in FIG. 1. The Y-shaped coupler 982 may have a gas sampling port 982b which may be configured as the same as described in the first embodiment of the present invention. In at least one embodiment, there is no gas sampling port on the coupler 982. An adaptor with a gas sampling port (not shown) may be attached to the outlet 982a of the coupler 982 for gas sampling if needed.

A left delivery tube (a left inner tube) 915 is positioned inside the left breathing tube 907 and a right delivery tube (a right inner tube) 914 is positioned inside the right breathing tube 906, defining inner lumens (a left inner lumen and a right inner lumen) of the breathing tubes 907 and 906. The spaces surrounding the delivery tubes 915 and 914 define outer lumens (a left outer lumen and a right outer lumen) of the breathing tubes 907 and 906. The delivery tubes 915 and 914 can be a corrugated flexible tube or a straight tube without any corrugations. However, a corrugated configuration is preferable because it provides a good flexibility and prevents collapse. A first end 915a of the left delivery tube 915 is laterally connected to a first end 916g of the inner central tube 916 and a first end 914a of the right delivery tube 914 is laterally connected to a second end 916h of the inner central tube 916. The left and the right delivery tubes 915 and 914 are made integral with the inner central tube 916 to form into a single tube so that there are no connection elements between the delivery tubes 915 and 914 and the inner central tube 916. The first end 916g of the inner central tube 916 is also the first end 915a of the left delivery tube 915. The connecting point of the inner central tube 916 and the delivery tube 915 is indicated as 916g and 915a, which may be located at the same or substantially the same location in FIG. 13. The second end 916h of the inner central tube 916 is also the first end 914a of the left delivery tube 914. The connecting point of the inner central tube 916 and the delivery tube 914 is indicated as 916h and 914a, which may be located at the same or substantially the same location in FIG. 13. A second end 915b of the left delivery tube 915 and a second end 914b of the right delivery tube 914 are connected to a Y-shaped connector 980. The Y-shaped connector 980 is positioned inside the coupler 982 with a gas supplying port 980a which is configured in a way that a gas supplying tubing or hose or a standard anesthesia circuit can be attached.

The coupler 982 has a half ring or D-ring 982c (identical to 12c of FIG. 2A) or the like. A strap 940 has one end which is attached to the half ring or D-ring 982c or the like and another end which is attached to a badge clip 942 or the like. The badge clip 942 or the like is attached to the clothes of the user for supporting the breathing tubes 906 and 907 (including the delivery tubes 914 and 915) and the coupler 982.

The inner central tube 916 may have a same size or a different size as the delivery tubes 914 and 915. The inner central tube 916 and the central tubular chamber 904 may have a same length L9 shown in FIG. 13. The inner diameter of the inner central tube 916 is preferably about one third to half of the inner diameter of the central tubular chamber 904. The inner central tube 916 defines a second chamber of the central tubular chamber 904. The space surrounding the inner central tube 916 defines a first chamber of the central tubular chamber 904. A bottom wall of the inner central tube 916 is directly attached to the bottom wall of the central tubular chamber 904. As an alternative, the inner central tube 916 can be attached to the inner wall of the central tubular chamber 904 via a few support rods or the like as shown in FIG. 2A, so that the inner central tube 916 will not move within the central tubular chamber 904. Both the breathing tubes 906 and 907 and the delivery tubes 914 and 915 are made from silicone, polypropylene, or the like. They are highly flexible, lightweight, crush-resistant, and/or semi-transparent or transparent. The inner diameter of each of the delivery tubes 914 and 915 is about one third to half of the inner diameter of the corresponding breathing tubes 906 and 907, so that the air flow from the first chamber of the central tubular chamber 904 can be discharged through the outer lumens of the breathing tubes 906 and 907 during exhalation without significant resistance. In at least one embodiment, the inner diameter of each of the delivery tubes 914 and 915 is about half to two thirds of the inner diameter of the corresponding breathing tubes 906 and 907, so that the delivery tubes 914 and 915 will be used for discharging gases and the outer lumens of the breathing tubes 906 and 907 will be used for delivering gases. There are two holes or two ports 916a and 916b on a top wall of the inner central tube 916. Each of the two holes or ports 916a and 916b is axially aligned with the corresponding openings of the top wall of the central tubular chamber 904 to direct air flow from the inner central tube 916 toward the corresponding nasal sealing members 910 and 908. The holes or ports 916a and 916b are configured as the same as described in the first embodiment of the present invention.

Figure 14:
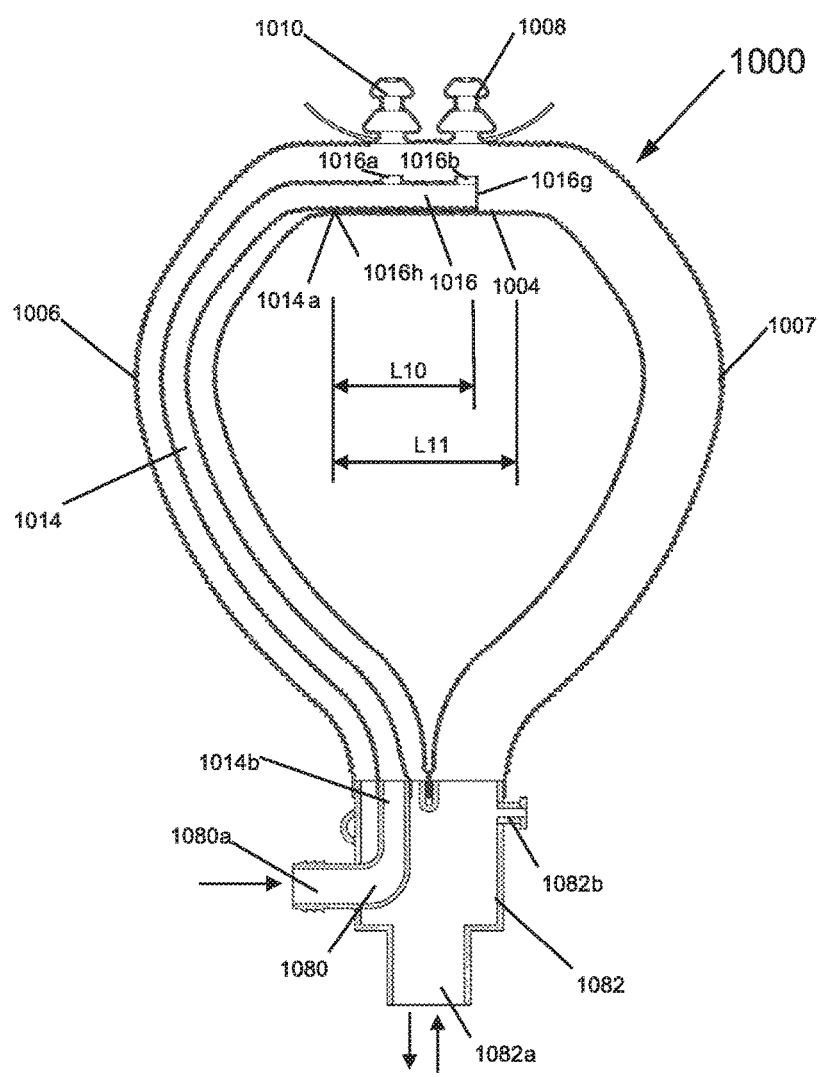
FIG. 14 shows a simplified diagram of a front cross-sectional view of part of the nasal breathing apparatus, somewhat different from that in FIG. 12, in accordance with another embodiment of the present invention.

In various embodiments, the device has only one delivery tube 1014 that is positioned inside the right breathing 1006 as shown in FIG. 14. FIG. 14 shows an apparatus 1000 which may be the same as what is shown in FIG. 13, except as will be described. The apparatus 1000 includes an inner central tube 1016, which has a first end 1016g and a second end 1016h opposite to the first end 1016g. There are two holes or two ports 1016a and 1016b (identical to 916a and 916b of FIG. 13) on a top wall of the inner central tube 1016. The holes or ports 1016a and 1016b are configured as the same as described in the first embodiment of the present invention. The length L10 of the inner central tube 1016 may be equal to or shorter than the length L11 of the central tubular chamber 1004. The first end 1016g of the inner central tube 1016 is a closed end. The second end 1016h of the inner central tube 1016 is connected to a first end 1014a of a delivery tube (an inner tube) 1014 and there are no distinct connecting points between them. The connecting point of the inner central tube 1016 and the delivery tube 1014 is indicated as 1016h and 1014a, which may be located at the same or substantially the same location in FIG. 13. The inner diameter of the delivery tube 1014 can be made in a bigger size so that it can allow to deliver high flow of gases. Since there is no delivery tube inside a left breathing tube (a left outer tube) 1007 and a right breathing tube (a right outer tube) 1006 that has a delivery tube 1014 inside also allows to discharge gases, the exhaled gases can be discharged more easily with this embodiment. A second end 1014b of the delivery tube 1014 is connected to a curved tube 1080 (similar to a curved tube 12d in FIG. 2A) that is positioned inside the coupler 1082. The gas supplying port 1080a, the outlet 1082a, and the gas sampling port 1082b are similar or identical to 980a, 982a, and 982b of 900 of FIG. 13, respectively. The apparatus 1000 includes nasal sealing members 1010 and 1008.

Figures 15A, 15B, 15C, 15D:
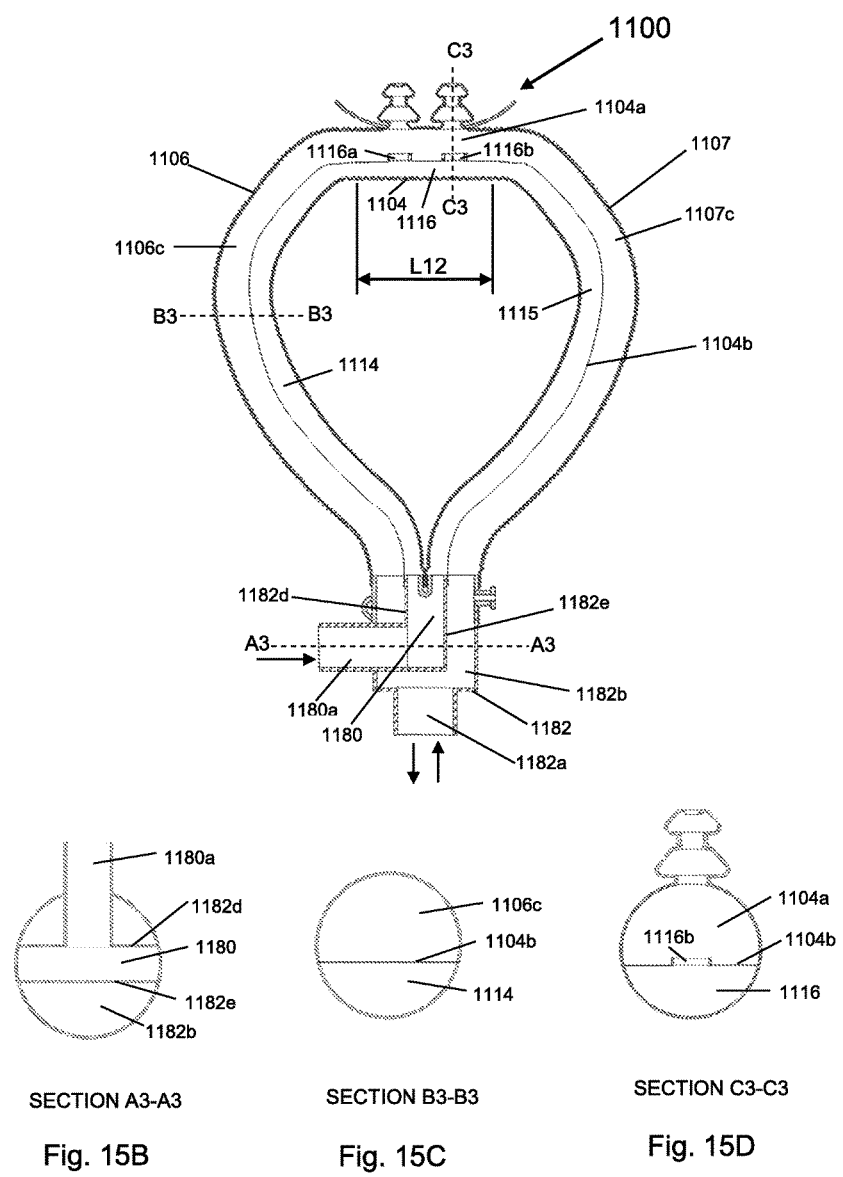
FIG. 15A shows a simplified diagram of a front cross-sectional view of part of the nasal breathing apparatus, somewhat different from that in FIG. 12, in accordance with another embodiment of the present invention.
FIG. 15B shows a cross-sectional view of the nasal breathing apparatus of FIG. 15A along a line A3-A3.
FIG. 15C shows a cross-sectional view of the nasal breathing apparatus of FIG. 15A along a line B3-B3.
FIG. 15D shows a cross-sectional view of the nasal breathing apparatus of FIG. 15A along a line C3-C3.

In various embodiments, the device of FIGS. 12-13 has no inner central tube within central tubular chamber and has no inner tubes inside breathing tubes (outer tubes) 1107 and 1106 as shown in FIG. 15A. FIG. 15A shows an apparatus 1100 which may be the same as what is shown in FIG. 13, except as will be described. An inner septum or partition 1104b segregates the central tubular chamber 1104 into a first chamber 1104a and a second chamber 1116, and the breathing tubes 1107 and 1106 into breathing lumens 1107c and 1106c and delivery lumens 1115 and 1114 respectively, as shown in FIGS. 15A-D. The inner septum 1104b starts from a coupler septum or partition 1182d, extends lengthwise along the breathing tube 1106, the central tubular chamber 1104, and the breathing tube 1107 and terminates at another coupler septum or partition 1182e. Both the first chamber 1104a and the second chamber 1116 have a same length L12. The first chamber 1104a (equivalent to a first chamber of the central tubular chamber 904 of FIG. 13) is in fluid communication with the breathing lumens 1107c and 1106c (equivalent to outer lumens of the breathing tubes 907 and 906 of FIG. 13) and the second chamber 1116 (equivalent to a second chamber of the central tubular chamber 904 of FIG. 13) is in fluid communication with the delivery lumens 1115 and 1114 (equivalent to inner lumens of the breathing tubes 907 and 906 of FIG. 13). The second chamber 1116 is in fluid communication with the first chamber 1104a of the central tubular chamber 1104 via two holes or ports 1116a and 1116b (similar or identical to 916a and 916b of FIG. 13) which are located a top wall of the second chamber 1116. The top wall of the second chamber 1116 is a part of the inner septum 1104b, which is also a bottom wall of the first chamber 1104a. The two holes or ports 1116a and 1116b are configured as the same as described in the first embodiment of the present invention. The breathing tubes 1107 and 1106 are connected to a Y-shaped coupler 1182. The coupler septa 1182d and 1182e segregate the coupler 2082 into a breathing passage 1182b and a delivery passage 1180. The breathing passage 1182b is in fluid communication with the breathing lumens 1107c and 1106c and the delivery passage 1180 is segregated from the breathing passage 1182b and in fluid communication with the delivery lumens 1115 and 1114. The ratio of the cross-sectional area of the first chamber 1104a and the cross-sectional area of the second chamber 1116 of the central tubular chamber 1104 and the ratio of the cross-sectional areas of the breathing lumens 1107c and 1106c and the cross-sectional areas of the delivery lumens 1115 and 1114 can be varied according to the need for their main functions. For example, the breathing lumens 1107c and 1106c may have smaller cross-sectional areas if the device is mainly made for CPAP therapy. The smaller breathing lumens will provide a fixed resistance to exhalation flow. If the device is mainly made for delivering gases, the breathing lumens 1107c and 1106c may have larger cross-sectional areas so that the patient can breathe more easily without significant resistance during spontaneous respiration. The outlet 1182a and the gas supplying port 1180a are similar or identical to 982a and 980a of 900 of FIG. 13, respectively. The nasal interfaces of the embodiments of FIG. 15A will be more compact and lightweight compared to the nasal interfaces of the embodiments of FIGS. 12 and 13 and has all functions as the nasal interfaces of the embodiments of FIGS. 1-14.

In various embodiments, the device of 1000 of FIG. 14 has no inner central tube within central tubular chamber 1204 and has no delivery tube within a left breathing tube (a left outer tube) 1207 as shown in FIG. 16. FIG. 16 shows an apparatus 1200 which may be the same as what is shown in FIG. 14, except as will be described. An inner septum or partition 1204b segregates the central tubular chamber 1204 into a first chamber 1204a and a second chamber 1216, and a right breathing tube (a right outer tube) 1206 into a breathing lumen 1206c and a delivery lumen 1214 as shown in FIG. 16. The length L13 of the second chamber 1216 may be equal to or shorter than the length L14 of the central tubular chamber 1204. The second chamber 1216 is in fluid communication with the first chamber 1204a of the central tubular chamber 1204 via two holes or ports 1216a and 1216b (similar or identical to 1016a and 1016b of FIG. 14) which are located on a top wall of the second chamber 1216. The top wall of the second chamber 1216 is a part of the inner septum 1204b, which is also a bottom wall of the first chamber 1204a. The two holes or ports 1216a and 1216b are configured as the same as described in the first embodiment of the present invention. The first chamber 1204a is in fluid communication with a right breathing lumen 1206c and a left breathing tube 1207. The second chamber 1216 (equivalent to an inner central tube 1016 of FIG. 14) has a first end which is in communication with a right delivery lumen 1214 and a second end which is closed by a side wall or septum 1216g. The inner septum 1204b extends lengthwise from the side wall 1216g of the second chamber 1216 and terminates at a coupler septum 1282d. The coupler septum 1282d and another coupler septum 1282e of the coupler 1282 segregate the coupler 1282 into a breathing passage 1282b and a delivery passage 1280. The outlet 1282a and the gas supplying port 1280a are similar or identical to 1082a and 1080a of 1000 of FIG. 14, respectively. The nasal interfaces of the embodiments of FIG. 16 will be more compact and lightweight compared to the nasal interface of the embodiment of FIG. 14 and has all functions as the nasal interfaces of the embodiments of FIGS. 1-15.

The nasal interfaces of the embodiments of FIG. 12-16 of the present invention have all functions as the nasal interfaces of the embodiments of FIGS. 1-4, the embodiments of FIGS. 5-6, and the embodiments of FIGS. 7-11 of the present invention. For description purpose, only the functions of the apparatus 900 of the embodiment of FIGS. 12 and 13 is explained. When the nasal interface of FIG. 12-13 is used for delivering gases and CPAP, the gas supplying port 980a is connected to a gas supplying source via a gas supplying tubing, or a conduit. The fresh gas from the connector 980 is delivered to the nasal airway through the left and the right delivery tubes 915 and 914, the inner central tube 916, the first chamber of the central tubular chamber 904, and the nasal sealing members 908 and 910. The exhaled gas is discharged to ambient through the nasal sealing members 908 and 910, the first chamber of the central tubular chamber 904, the outer lumens of the left and the right breathing tubes 907 and 906, and the outlet 982a and sampled through the sampling port 982b. If needed, a non-rebreathing tee adaptor 7 shown in FIG. 2C or a vent tube 3 shown in FIG. 2B can be attached to the outlet 982a of the coupler 982. When the nasal interface is used for NIV or rescue breathing, an anesthesia circuit or a resuscitator bag can be connected to the outlet 982a of the coupler 982 with the gas supplying port 980a being blocked or to the gas supplying port 980a with the outlet 982a of the coupler 982 being blocked. During spontaneous respiration, rebreathing will not occur with adequate fresh gas flow. During mechanical ventilation, the effects of the added anatomic dead space from the outer lumens of the breathing tubes 906 and 907 can be easily reduced or overcome by increasing minute ventilation or by increasing fresh gas flow. Since the device or apparatus 900 has two outer lumens for discharging exhaled gases, there will be less resistance during expiration. The patient will feel more comfortable because airflow is not impeded during inspiration and expiration. The same breathing device can be used for delivering low flow or high flow of gases, monitoring end tidal $CO_2$, and providing CPAP and positive pressure ventilation. No patient interface change is needed.

In various embodiments, the nasal breathing apparatuses of FIGS. 1-16 may have only one nasal sealing member and the inner central tube (or the second chamber) may only have one hole on its top wall, so that only one nostril is sealed, and the other nostril is not sealed. The patient breathes through both nostrils, but gases delivery and ventilation are achieved through only one nostril. Although nasal sealing members, central tubular chamber, inner central tube, breathing tube(s), and delivery tube(s) are preferably made integral in one single piece and there are no connection elements, such as connectors or joints between them, they can be made separately and assembled or connected to form into one single piece by suitable means, such as connectors before use. For example, central tubular chamber, inner central tube, and nasal sealing members may be made integral as a single unitary component. This single unitary component can be connected to a breathing tube or a pair of breathing tubes and a delivery tube or a pair of delivery tubes just before use.

Although the invention has been described by reference to particular illustrative embodiments thereof, many changes and modifications of the invention may become apparent to those skilled in the art without departing from the spirit and scope of the invention. The nasal breathing apparatus of the present invention may be modified with appropriately reduced dimensions for neonates, infants, and children. It is therefore intended to include within this patent all such changes and modifications as may reasonably and properly be included within the scope of the present invention's contribution to the art.

I claim:

1. A nasal breathing apparatus comprising:
   a pair of nasal sealing members adapted to seal nostrils of a nose of a patient for delivering gases to and discharging gases from a nasal airway of the nose;
   a central tubular chamber that is integrally formed with each nasal sealing member of the pair of nasal sealing members and that has a first end which is a closed end and a second end opposite to the first end of the central tubular chamber;
   an inner central tube that is located inside the central tubular chamber and that has two ports which are axially aligned with the pair of nasal sealing members for delivering gases to the nasal sealing members and that has a first end which is a closed end and a second end opposite to the first end of the inner central tube and that defines a second chamber of the central tubular chamber;
   wherein a space surrounding the inner central tube defines a first chamber of the central tubular chamber;
   an outer tube that is integrally formed with the central tubular chamber and that laterally extends from the second end of the central tubular chamber and that defines an outer lumen of the outer tube in fluid communication with the first chamber of the central tubular chamber for conducting gases to and from the first chamber of the central tubular chamber;
   an inner tube that is positioned inside the outer tube and that has a same length as the outer tube and that is integrally formed with the inner central tube and that is extended laterally from the second end of the inner central tube and that defines an inner lumen of the outer tube in fluid communication with a second chamber of the central tubular chamber for delivering gases to the nasal airway of the nose via the second chamber of the central tubular chamber, the ports of the inner central tube, the first chamber of the central tubular chamber, and the nasal sealing members;
   a pair of side straps which are coupled to a head strap system and adapted to apply adjustable pressure on the nasal sealing members and the nose and a face of the patient; and
   a coupler for coupling the inner tube to a gas supplying source for delivering gases to the second chamber of the central tubular chamber via the inner lumen of the outer tube and for coupling the outer tube for conducting gases from and to the first chamber of the central tubular chamber via the outer lumen of the outer tube.

2. The nasal breathing apparatus of claim 1 further comprising a non-rebreathing tee adaptor for being connected to an outlet of the coupler and having a one-way inspiratory valve adapted to permit air flow enter the outer lumen of the outer tube during inhalation and a one-way expiratory valve adapted to permit expired gases be discharged from the outer lumen of the outer tube during exhalation and be capable of providing adjustable resistance to expiratory air flow.

3. The nasal breathing apparatus of claim 1 further comprising a vent tube for being connected to an outlet of the coupler and placed remote from the face of the patient for reducing noise level from expired gases of the outer lumen of the outer tube.

4. The nasal breathing apparatus of claim 1, wherein each of the nasal sealing members comprises a top portion which is formed in a mushroom shape, a base portion which is formed in a mushroom shape and is larger than the top portion in diameter, a spirally corrugated tube which connects the top portion to the base portion, and a short tube which connects the base portion to the central tubular chamber;

wherein the top portions are configured to be placed inside the patient's nostrils and thereby adapted to create a sealing interface inside the nostrils; and wherein the base portions are adapted to seal the openings of the patient's nostrils by forming physical sealing interfaces with the inner edges and the outer edges of openings of the corresponding nostrils when the top portions are placed inside the nostrils.

5. The nasal breathing apparatus of claim 1, wherein the central tubular chamber is a corrugated tube and adapted to be located beneath a nose and above an upper lip of a patient when worn by the patient;

wherein the first chamber of the central tubular chamber is in fluid communication with the nasal sealing members, the inner central tube, and the outer lumen of the outer tube;

wherein the central tubular chamber has a top wall and a bottom wall; and wherein the central tubular chamber, the nasal sealing members, and the outer tube are formed integrally as a single piece.

6. The nasal breathing apparatus of claim 1, wherein the inner central tube is positioned within the central tubular chamber at a location that is more nearer to the bottom wall of the central tubular chamber than to the top wall of the central tubular chamber;

wherein the inner central tube has a top wall;

wherein the two ports of the inner central tube are located on the top wall of the inner central tube and are aligned with the corresponding nasal sealing members; and wherein each of the ports of the inner central tube is configured to direct gases from the second chamber of the central tubular chamber to the corresponding nasal sealing members via the first chamber of the central tubular chamber.

7. The nasal breathing apparatus of claim 4, wherein each base portion of the nasal sealing members has a bottom which is connected to the top wall of the central tubular chamber by a short tube; and wherein the side straps are laterally extended from the short tubes respectively and positioned between the bottoms of the base portions of the nasal sealing members and the top wall of the central tubular chamber respectively and coupled to a head strap providing upward lift beneath the bottoms of the nasal sealing members.

* * * * *